(12) United States Patent
Discenzo

(10) Patent No.: US 11,786,147 B2
(45) Date of Patent: Oct. 17, 2023

(54) DISTRIBUTED SENSOR-ACTUATOR SYSTEM FOR SYNCHRONIZED MOVEMENT

(71) Applicant: Frederick Michael Discenzo, Brecksville, OH (US)

(72) Inventor: Frederick Michael Discenzo, Brecksville, OH (US)

(*) Notice: Subject to any disclaimer, the term of this patent is extended or adjusted under 35 U.S.C. 154(b) by 662 days.

(21) Appl. No.: 16/873,184

(22) Filed: Feb. 22, 2020

(65) Prior Publication Data

US 2020/0268287 A1 Aug. 27, 2020

Related U.S. Application Data

(60) Provisional application No. 62/810,090, filed on Feb. 25, 2019.

(51) Int. Cl.
*A61B 5/11* (2006.01)
*G06F 3/01* (2006.01)
*G06F 1/16* (2006.01)
*A61B 5/00* (2006.01)

(52) U.S. Cl.
CPC ............ *A61B 5/1126* (2013.01); *A61B 5/112* (2013.01); *A61B 5/1117* (2013.01); *A61B 5/1118* (2013.01); *G06F 3/016* (2013.01); *A61B 5/681* (2013.01); *A61B 2562/0219* (2013.01); *G06F 1/163* (2013.01)

(58) Field of Classification Search
CPC ... A61B 5/1117; A61B 5/1118; A61B 5/1126; A61B 5/112
See application file for complete search history.

(56) References Cited

U.S. PATENT DOCUMENTS

| | | | |
|---|---|---|---|
| 2014/0074179 A1* | 3/2014 | Heldman | G16H 50/50 607/45 |
| 2015/0077234 A1* | 3/2015 | Fullam | G04G 17/083 340/407.1 |
| 2015/0092980 A1* | 4/2015 | Folmer | G06V 40/165 382/103 |
| 2016/0206499 A1* | 7/2016 | Shim | A61F 2/70 |
| 2017/0225033 A1* | 8/2017 | Czaja | G06K 9/00496 |

(Continued)

FOREIGN PATENT DOCUMENTS

| CN | 105992554 A | * 10/2016 | ............ A61B 5/112 |
|---|---|---|---|
| KR | 101112497 B1 | * 5/2012 | ............ A63B 22/02 |

*Primary Examiner* — Kaylee R Wilson
*Assistant Examiner* — Raymond P Dulman

(57) ABSTRACT

Aspects describe capturing the dynamic movement of one or more leaders and generating stimulus signals in real time for one or more followers to perform substantially the same movement. A model of each follower is optionally employed to transform the observed movement of a leader to a series of movement cues that will overcome any follower physical and cognitive limitations while maximizing the movement compliance and benefit from the directed movement. Also provided is the capability of establishing a library of therapeutic, fitness, rehabilitation or dance movement scripts that may be replayed at the follower's convenience without a leader present. Additionally, one aspect provides for continually monitoring follower movement to detect unstable movement, an increased likelihood of a fall and gait anomalies and initiating a stimulus pattern to reduce the chance of a fall or injury.

29 Claims, 18 Drawing Sheets

(56) References Cited

U.S. PATENT DOCUMENTS

2017/0332946 A1* 11/2017 Kikkeri ................ A61B 5/1116
2018/0005616 A1*  1/2018 Gullbrand ............... G10H 1/40
2019/0053762 A1*  2/2019 Saigh .................... A61B 90/98

* cited by examiner

DISTRIBUTED SENSOR-ACTUATOR SYSTEM FOR SYNCHRONIZED MOVEMENT

TECHNICAL FIELD

The subject disclosure relates generally to providing cues to guide human movement toward more desirable body movement and more particularly to sensing desired human movement and adaptively providing stimulus cues to assist another person in performing a movement pattern that closely matches the more desirable or nominal movement pattern based at least in part upon sensors, actuators, distributed communications, modeling and prediction methods.

BACKGROUND

Since the early days of the Greeks and Chinese, the reported benefits of exercise have included good health, a good life and a prosperous life. Exercise has been shown to improve the recovery rate from injury or surgery and also to help prevent injury such as from a fall. Exercise has also been shown to provide significant cognitive benefits for older adults. A sedentary lifestyle increases the risk of all-cause mortality, cardiovascular disease and death from cardiovascular disease and type 2 diabetes along with an increased risk of colon, endometrial and lung cancers. The U.S. Department of Health and Human Services states that adults need at least 150 minutes of moderate-intensity physical activity each week. (PhysicalActivityGuidelinesforAmericans, $2^{nd}$ edition, health.gov/PAGuidelines). Roughly one-half of adults do not even meet this minimum level of weekly exercise. It is particularly important for older adults and those with physical limitations including chronic conditions such as Parkinson's disease and multiple sclerosis to achieve the recommended 150 minutes of moderate to rigorous exercise weekly to the extent they can do it safely and within their fitness limits. Exercise, physical movement and dance have been shown to provide important benefits for this population.

Many older adults and people with injury or chronic neurological conditions are at an increased health risk since they do not exercise as much as they should. Unfortunately, older adults, individuals with neurodegenerative diseases and cognitive impairment frequently exercise much less than the average population, yet exercise is even more important for these people. Physical inactivity as well as biological aging results in a decrease in maximum muscle force and also a reduction in the rate of force development (RFD). The reduction in RFD is critically important for reducing falls yet it decreases faster than maximum muscle force with aging and lack of exercise.

Regular exercise, therapeutic movement and dance can enhance the health and quality of life for many people including older adults, people recovering from injury or surgery and people with chronic neurological conditions or movement disorders. Dance provides a wide range of benefits including aerobic benefits, improvement in balance and posture, cognitive benefits and social benefits. Multiple studies of dance show compelling benefits for people with Parkinson's disease and Alzheimer's disease. Dance also provides significant cognitive benefits for older adults (adults 65 years old and older). These reasons for not exercising include limited range of motion (extension or flexion), slowness of motion (bradykinesia), inability to follow prescribed exercise patterns, confusion and cognitive deficiencies, social pressures from participating in group exercise or dance classes and lack of timing and coordination. Participating in a group exercise or dance class requires attention, focus and coordination to observe and perform the directed movements. Limitations in understanding observed movement, internalizing viewed movement to cause similar self-movement and the inability to recall prescribed movement patterns prevents many from realizing the benefits of exercise, therapeutic movement and dance.

According to the US Centers for Disease Control and Prevention only 53.3% of adults over 18 meet the Physical Activity Guidelines for aerobic physical activity and less than 24% meet the Physical Activity Guidelines for both aerobic and muscle strengthening activity (https://www.cdc.gov/nchs/fastats/exercise.htm). While performing exercise and dance for people with Parkinson's disease, multiple sclerosis and Alzheimer's is particularly difficult, the benefits exercise and dance provides to this population has been shown to be significant in delaying disease progression, reducing the chance of falling and improving the quality of life.

SUMMARY

The following presents a simplified summary in order to provide a basic understanding of some aspects of the subject disclosure. This summary is not an extensive overview and it is not intended to identify key or critical elements of all aspects nor delineate the scope of any or all aspects. The sole purpose of this summary is to present some concepts of one or more aspects in a simplified form as a prelude to the more detailed description that is presented later.

An aspect relates to a system that facilitates movement by a person in a more beneficial or desirable manner than would have occurred without the system. The system comprises a sensor, processor, communications and actuator configured in a manner to detect movement from the first person and then energize an actuator to cause a second person to duplicate the movement performed by the first person. The process includes continuously monitoring movement from the first person and immediately energizing the appropriate actuator(s) to guide a second person to perform the same motion concurrent with the motion of the first person. Wearable sensors, actuators and processors may be employed along with wireless communications managed by real time software operating in a micro-controller. Also included in the system are software algorithms that interpret sensed motion of the first person and generate a control action to energize one or more actuators worn by the second person that direct the second person to move their body and/or limbs in a manner mirroring the first person.

Another aspect relates to sensing the desired movement of a leader, generating a stimulus pattern to guide a person to duplicate the desired motion and then broadcasting the stimulus pattern in real time to multiple receiving people such as in a group class setting. Whereby, each person receiving the same stimulus pattern will simultaneously perform the desired movement prescribed by the leader.

Yet another aspect relates to adaptively modifying the stimulus signal for each person in a manner consistent with the person's motor skill level, balance, cognitive abilities and sensory response. Modifications many employ predictive modeling and iterative closed-loop stimulus in order to meet an objective such as close compliance with the desired motion in a safe manner, greater therapeutic benefit, increased range of motion, improved gait or improved balance for example.

Still another aspect relates to monitoring the person's actual movement and then continually modulating the stimulus signal provided to help insure movement is as spatially and temporally correct as possible for each unique individual and to help promote learning. As movement performed more closely matches the desired, target movement, stimulus signals will be reduced and eventually stimulus signals will only be used when needed to correct errors.

Still another aspect relates to storing the desired movement patterns on a persistent storage device such as a hard disk drive or non-volatile memory such as a solid state drive. The stored desired movement patterns are then recalled at a later time and used to generate dynamic stimulus signals to cause people receiving the stimulus signals to move in a manner that closely matches the previously stored movement pattern(s).

To the accomplishment of the foregoing and related ends, one or more aspects comprise features hereinafter fully described. The following description and annexed drawings set forth in detail certain illustrative features of one or more aspects. These features are indicative, however, of but a few of various ways in which principles of various aspects may be employed. Other advantages and novel features will become apparent from the following detailed description when considered in conjunction with the drawings and the disclosed aspects are intended to include all such aspects and their equivalents.

DETAILED DESCRIPTION

An assistive device that can guide a person in performing exercise, therapeutic movement or dance in a low-cost non-invasive manner can help millions of people realize greater levels of exercise, improved recovery, reduce chance of medical problems and improved quality of life. An adaptive, wearable device can help many people with neurological conditions such as Parkinson's disease, Huntington's disease, multiple sclerosis and Alzheimer's disease more fully realize the significant benefits that have been shown from exercise and dance.

Various aspects are now described with reference to the drawings. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing these aspects.

Figure 1:
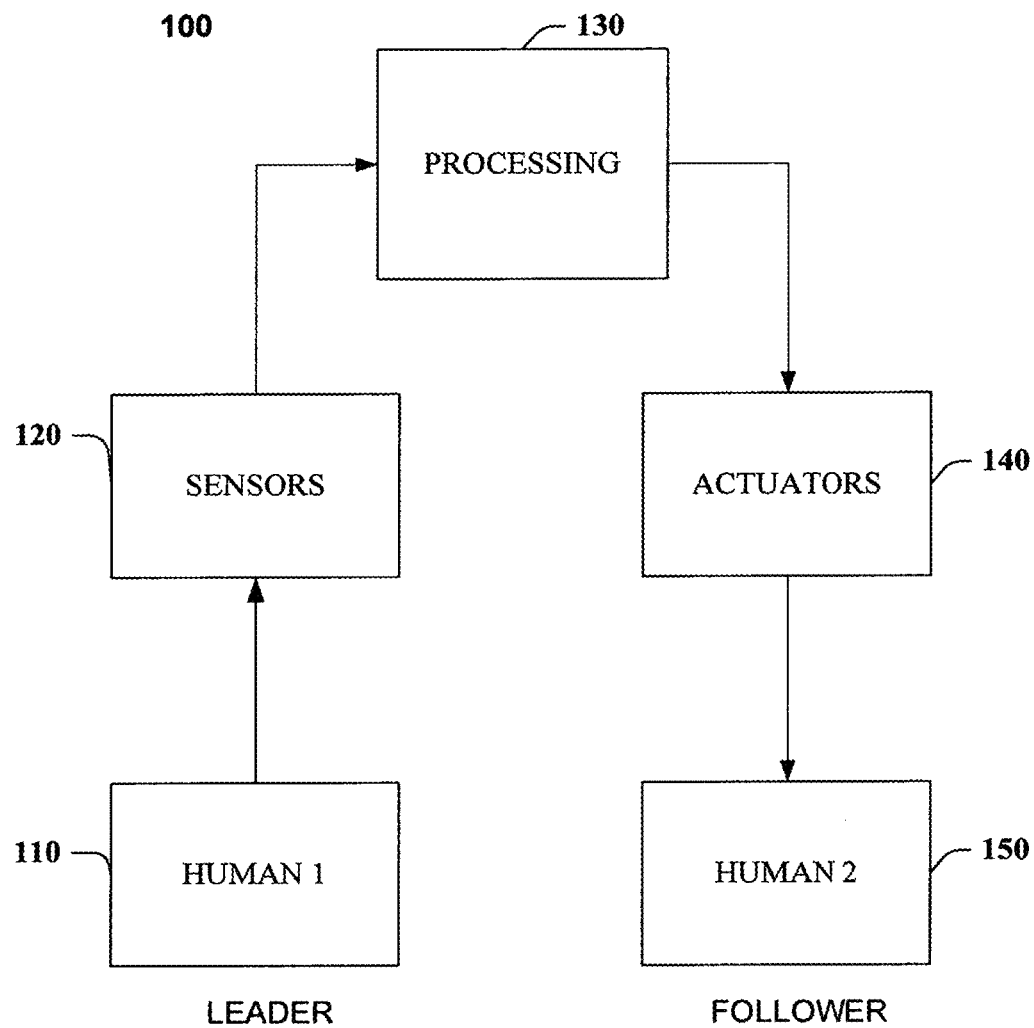
FIG. 1 illustrates a conceptual model of the movement synchronization process, according to an aspect.

Turning now to the figures, FIG. 1 illustrates a representative process 100, according to an aspect. This figure shows a conceptual model of motion sensing and motion synchronization. Movement from a human leader 110 is sensed by one or more motion sensors 120. Signals from the motion sensor(s) attached to 110 are periodically sampled by a processor 130. Processor 130 interprets these signals to determine what movement human leader 110 performed. The movement information may include information such as what appendage moved such as the left lower leg. Movement information determined by processor 130 may also include what direction appendage movement occurred, how fast movement occurred and how far the appendage moved. Computed appendage movement information is used by processor 130 to define which actuator(s) 140 to energize that will result in the human follower 150 moving the same appendage sufficiently in the same direction, same speed and same amount as human leader 110.

Sensors 120 may be wearable sensors attached to the body on leader 110 and in close proximity to the surface of the skin in a manner to facilitate detecting movement kinematics of leader 110. Similarly, actuators 140 may be wearable actuators on the body of the follower 150 and in close proximity to the surface of the skin in a manner to facilitate the follower 150 feeling the movement of actuators 140. Details describing sensor and actuator technologies and requirements for wearing these devices are presented later.

Processor 130 will periodically sample the movement sensor(s) attached to the leader 110. Following filtering, the sensor response is interpreted to define the desired kinematic movement of the leader 110. The movement of the leader 110 is used by processor 130 to determine what actuators need to be energized and when they need to be energized. The appropriate actuators attached to the follower 150 are then energized in a manner to stimulate or guide the follower 150 to take the same movement just performed by the leader 110.

The process of sensing, interpreting and energizing/de-energizing actuators proceeds in real time. The result is that the follower will continuously duplicate the movement of the leader as the leader moves different appendages, moves multiple appendages concurrently, moves at different speeds and moves an appendage in different amounts and different directions. Movement mirroring or synchronization provided by the operation of system 100 can proceed without the follower 150 seeing or hearing the leader.

Figure 2:
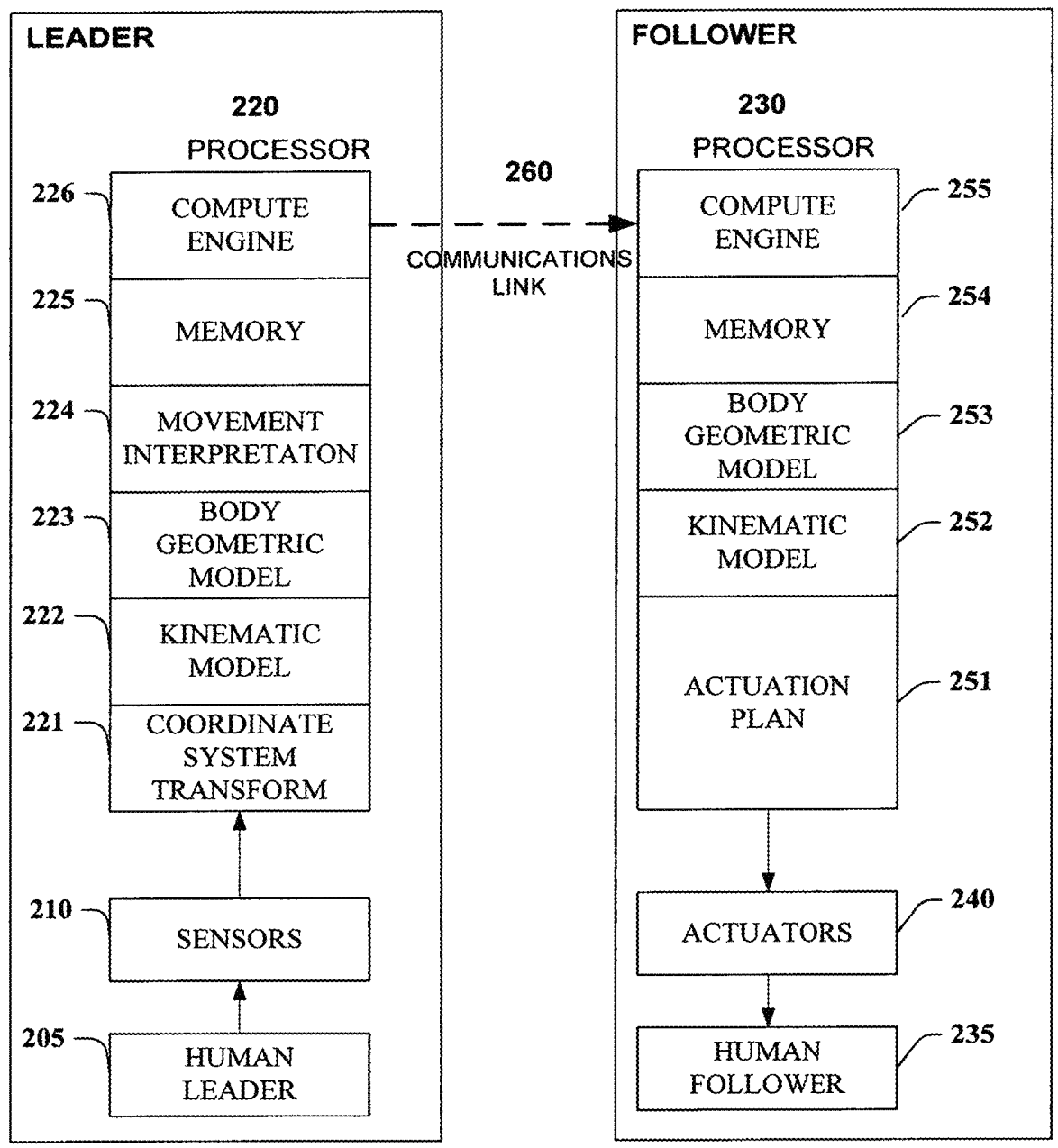
FIG. 2 illustrates a high-level overview of an example system that utilizes multiple processors, according to an aspect.

FIG. 2 illustrates a realization of movement synchronization system 200 where the leader 270 and follower 280 each have their own processors 220 and 230 respectively attached to their bodies as wearable devices. Processors 220 and 230 exchange data via communications link 260. The communications link 260 may be a wireless link such as Bluetooth or Wi-Fi for example. Sensors 210 are located on the body of leader 205 and processor 220 periodically interrogates or samples data from the sensor(s) 210. Processor 220 interprets the sampled sensor signals and determines kinematic movement patterns of the human leader 205. The determined nominal or desired movement kinematics of the leader 270 are communicated via the communications link 260 to processor 230 worn on the body of follower 280. Processor 230 analyzes the desired movement kinematics and determines which actuator or actuators 240 need to be energized in order to stimulate or direct movement of follower human 235 to substantially to perform the desired kinematic movement initially defined by leader human 205.

The process of periodically sampling and interpreting the sensor signals and generating a sequence or script of which actuators to energize is performed repeatedly in real-time in order to permit the follower to duplicate movement of the leader in synchrony and at nearly the same time. Interpreting sensor signals and defining which actuators to energize and when to energize them may be facilitated by the use of software models in the memory of each processor.

Interpreting signals from motion sensors such for example from accelerometers that provide data in X, Y and Z direction(s) relative to the sensor housing (e.g. triaxial accelerometer) involves transforming the sampled data into a common coordinate system. An absolute coordinate system can facilitate real-time sensing and control of multiple humans (e.g. leader and follower). An example absolute spatial reference system that is often used in kinematic studies defines the three directions of human body. Vertical direction is Y direction, forward and back is X direction and side to side is Z direction. Consistent with common naming practices then, a YZ plane is called the frontal plane, an XZ plane is called the transverse plane and an XY plane is called the sagittal plane. Data analysis may done using this coordinate system; however, any suitable spatial coordinate scheme is contemplated and can be employed. A software model for transforming data into and out of this coordinate system can be located in the processor of the leader and follower.

In one example, a set of model-based software routines and algorithms are embedded in the processor 220 of the leader to facilitate interpreting the raw sensor data. Similarly, a set of model-based software routines and algorithms are embedded in the processor of the follower 230 to facilitate translating the observed leader movement to movement appropriate for the follower and defining a sequence of specific actuators to be energized that will likely result in the follower duplicating the movement observed by the leader. For example, software algorithms used to interpret the sensor signals on the leader may include a coordinate transformation module 221, a kinematic model 222, a geometric model of the leader 223 that includes information such as body dimensions of the leader and a movement interpretation model 224. Some movements of the leader may not need to be duplicated and may distract the follower from following the main movement desired. These models and other software used by the compute engine 226 may reside in local memory 225 integral to processor 220.

Continuing the above example, processor 230 worn by the follower 280 may contain software models and algorithms to facilitate interpreting the desired movement of the leader into terms that relate to desired movement of the follower and then into a plan or script of sensor actuation that will ultimately result in the follower moving their body parts at the correct time, speed and distance that matches movement of the leader sufficiently close. It will be effective to utilize a body geometric model 253 that translates the movement of the leader to the desired movement of the follower while accommodating for differences in body size between the leader and follower including differences in upper and lower leg length as well as other limb length differences and body size differences. Upon determining the follower movement required, a kinematic model 252 of the follower may be employed to determine which appendages should be directed for movement. For example, to duplicate the leader's step movement, a small step may only require directing the lower leg to move while duplicating a large step may require directing that the upper thigh move a certain amount and the lower leg move a different amount. Upon determining how each appendage should move, an actuation planning module 251 can map the desired movement to specific actuators worn by the leader and define a script that specifies which actuators 240 need to be energized, when each one should be energized and the duration each actuator should be energized.

Figure 3:
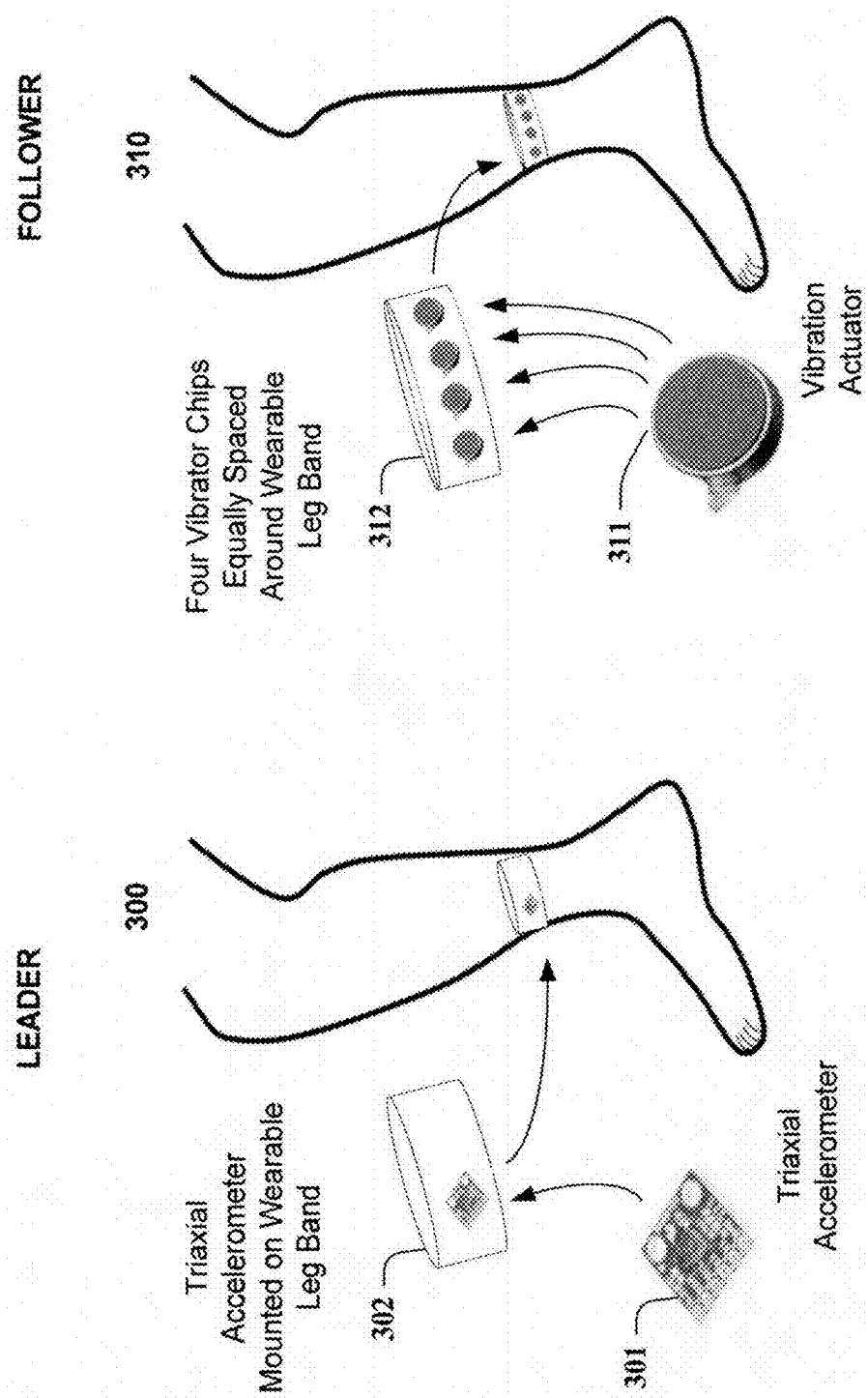
FIG. 3 illustrates an example of one sensor and set of actuators attached to a leg to direct leg movement of a second leg, according to an aspect.

Turning now to FIG. 3. The diagram shows an example of how a sensor and set of actuators may be attached to a lower leg. In this example, movement of the lower leg 300 of the leader is detected from the signal provided by an accelerometer 301 attached to a lower leg and attached in close proximity to surface of the leg. An accelerometer attached to the wearer in this manner will provide a clear movement signal without distortion due to the sensor slipping or moving due to layers of clothing. One implementation is to utilize a sensor with three integrated accelerometers packaged with the axis of each accelerometer orthogonal to the axis of the other two accelerometers 301 (e.g. triaxial accelerometer). The transformation of the sampled sensor data to the absolute, body-reference coordinate system described previously will accommodate for the axis of each sensor element not being perfectly aligned with the axis of the absolute coordinate system. The sensor may be attached to the appendage in a variety of ways including integrating the sensor into a cloth strap 302 and attaching the strap to the body with a Velcro® closure. The use of an accelerometer or triaxial accelerometer is described here. Other sensors and technologies to detect movement may be used such as ultrasonic sensors, piezo-electric based compliance sensors, fiber optic sensors, EMG sensors, static electric field sensing, liquid droplet motion sensors and video image processing for example. Furthermore, multiple sensors or multiple sensor modalities may be employed together to provide a more accurate or more complete assessment of the leader's movement and current position.

Continuing with FIG. 3, the follower receives cues in real-time to direct movement of the body or appendage(s). One method to provide cues to the follower to initiate movement is to attach small vibrating elements 311 to the follower. Upon being energized, the element vibrates signaling the wearer that movement needs to occur. In the example shown in FIG. 3, multiple vibration elements 311 are configured, evenly spaced around a cloth strap 312. The cloth strap 312 is attached to the lower leg 310 of the follower. The cloth strap is securely attached to the appendage of the follower to ensure that the wearer can clearly and quickly detect the presence of a vibration signal as well as the location of the vibration signal against the body. The strap with multiple integrated vibration devices may be attached using a Velcro® closure. In FIG. 3, four vibration elements 311 are evenly spaced around a cloth strap 312 that is attached to the lower leg 310. One orientation for attaching the strap with evenly spaced vibration elements is to have one vibration element toward the front of the leg, one vibration element toward the back of the leg, and vibration elements to each side of the leg. A stimulus signal provided to the wearer by the vibration of the vibrating elements will signal the wearer to move the leg 310 in the direction of the sensed vibration and at the time vibration is sensed for example. Movement may continue until the desired leg destination is reached for example. With only four vibrating elements, it is possible to signal movement not only forward and back and left and right, but also cues for diagonal motion may be provided. One way to provide this is to energize multiple vibration elements simultaneously that lie closest to the direction where movement is desired. Another option is to sequence the activation of the vibration elements. For example, movement diagonally forward to the right may be signaled by first energizing the forward facing vibration element, turning this element off and then quickly energizing the vibration element to the side. Alternatively, the signal to a vibration element may be modulated such as by providing a rapid sequence of on-off pulses. This will rapidly energize and de-energize the vibration element. The ratio of "on" time to "off" time can provide for varying the intensity of the vibration signal sensed by the wearer. A pulse width modulation (PWM) signal controlling the voltage to a vibrating element can be changed as needed and will be effective in communicating the strength of the vibration signal sensed by the wearer. A PWM signal is commonly used for rapidly sequencing an electrical device on and off such as for variable speed motor control. A PWM output signal is available on many microcontroller and microprocessor devices. Energizing multiple vibration elements and adjusting the intensity of the vibration signal can provide effective signaling information to guide the follower in moving the leg in the direction of both vibration elements but more closely aligned with the direction signaled by the vibration element with the stronger signal. Rather than using four discrete vibration elements, additional vibrating elements such as 8 or 16 or more vibration elements evenly spaced around the body or appendage of the wearer may be used to provide a clearer or stronger movement signal and more precise movement direction information to the follower. Alternatively, precisely controlling the stimulus of several actuators concurrently may enable movement cues to be provided with only three actuation devices. Actuation devices such as micro-motors with an eccentric mass, coin micro-motors and pancake micro-motors may also be used. Linear resonant actuators (LRA) devices 311 may also be used. LRA devices are small disk-shaped electrical actuators that operate like a voice coil and rapidly move a mass along the central axis of the device. Other viable actuation technologies include layered piezo-electric actuators and FES (functional electrical stimulation) pads.

Figure 4:
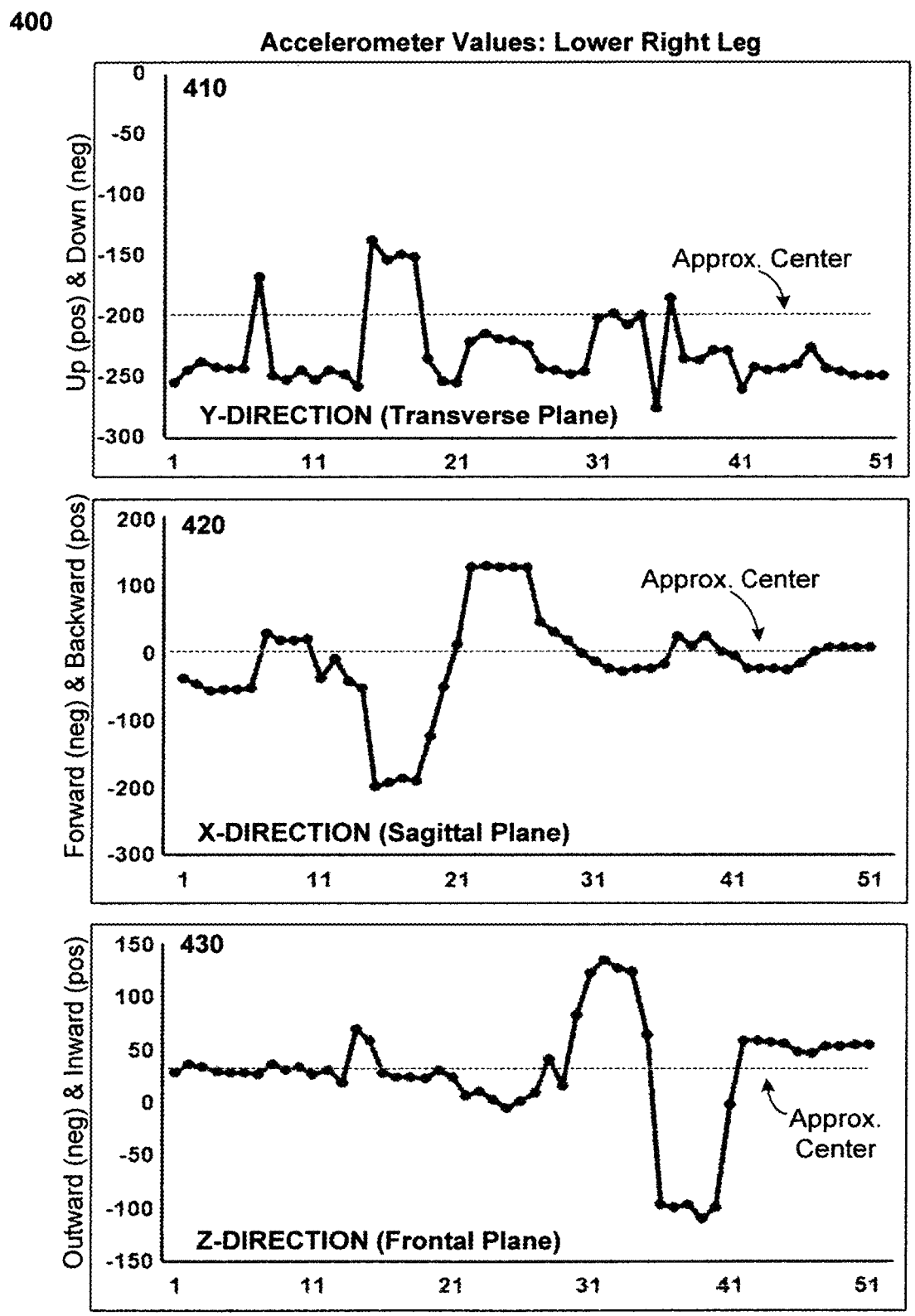
FIG. 4 illustrates data captured from a sensor attached to the lower right leg of a person, according to an aspect.

FIG. 4 presents three graphs of raw sensor data 400 captured from a triaxial accelerometer attached to the lower right leg of a test subject. The signal from the accelerometer is sampled once each second (1 Hz) and the sampled data for each orthogonal direction, X, Y, and Z is plotted on a separate axis 410, 420 and 430. Consistent with the absolute frame of reference defined above, the top graph 410 shows upward movement over time of the lower leg (Y-direction), the middle graph 420 shows forward movement over time of the lower leg (X-direction) and the bottom graph 430 shows sideways movement to the right, of the lower leg (Z-direction). Sampled movement data similar to the example shown in 400 is filtered and analyzed to determine what appendages moved, in what direction, at what rate and for how far. Inspecting the three graphs 410, 420 and 430 shows that the right leg of the tester first raised and the leg moved forward and then lowered as the leg moved back to the original position. The right leg then slid to the right and back to the original location without raising the leg. Commercial products that incorporate wireless sensors and provide kinematic movement data describing the wearer's movement in real time are available today (e.g. http://www.biosynsystems.net/, https://www.noraxon.com/).

Figure 5:
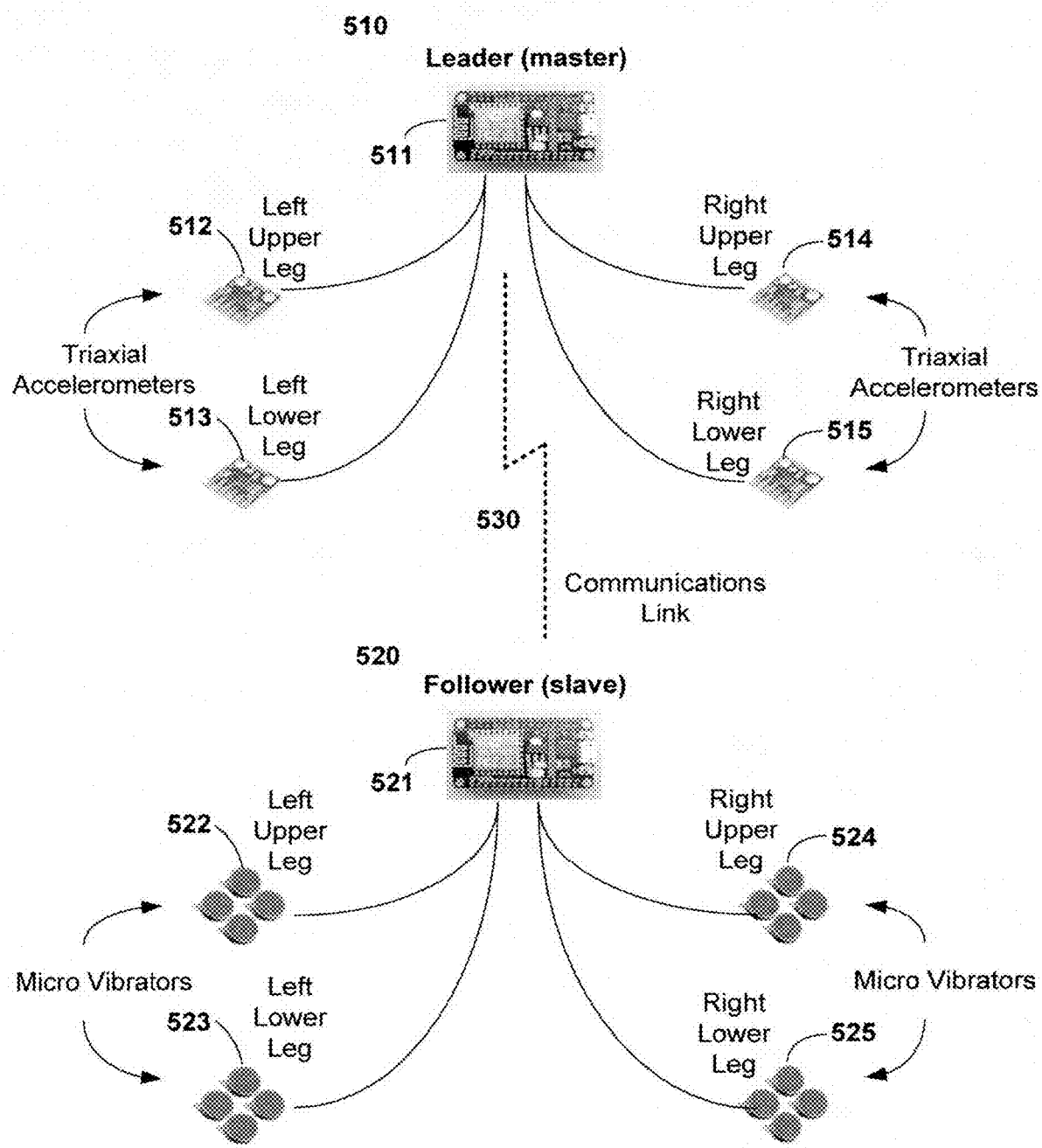
FIG. 5 illustrates an example configuration of sensors and actuators to direct movement of both legs for one person, according to an aspect.

An example hardware architecture for synchronizing motion with one leader 510 and one follower 520 is shown in FIG. 5. The diagram shows a single processor with embedded wireless radio for the leader 511 and one for the follower 521. Without loss of generality, the diagram shows four triaxial accelerometers on the leader, one each for the upper left leg 512, lower left leg 513, right upper leg 514 and lower right leg 515 with each sensor directly wired to inputs on the leader's microcontroller 511. Certainly additional sensors (e.g. accelerometers) could be attached to the leader to detect movement of the torso, arms, hand, head, shoulders and feet. Additionally, gyroscopes, magnetometers, acoustic, ultrasonic, optical and other sensor types could also be incorporated to provide a richer, more accurate and more complete measurement of the body movement of the leader such as body rotation and body orientation for example. As shown in FIG. 5, data from each accelerometer 512, 513, 514 and 515 is sampled by the processor 511. Data from each sensor is sampled concurrently and then input to signal processing algorithms resident in the leader's processor 511 to filter the raw data and extract kinematic movement data. Kinematic movement data along with timing information is transmitted to the follower's processor 521 with communications link 530. The wireless communications protocol can be Bluetooth (e.g. IEEE 802.15.1), Wi-Fi or wireless LAN (e.g. IEEE 802.11), radio broadcast (RF), PACS (Personal Access Communication System—used for cordless telephone systems) or ZigBee for example. Issues including physical hardware size, power requirements, transmission rate, accuracy, error correction, noise immunity, security and safety are important consideration to insure effective and reliable real-time leader-follower communications is supported.

The example hardware architecture shown in FIG. 5 provides a single processor-radio device 511 for the leader with all sensors hardwired to the input of the processor. Certainly alternative hardware configuration options are possible. For example, each triaxial accelerometer could integrated with a small processor and radio. The processor-radio embedded with each triaxial accelerometer, not shown on the diagram, can periodically sample the sensor data at the sensor location. Sampled data from each accelerometer-processor-radio module can then be transmitted in real-time to a main processor-radio device 511 worn by the leader. The central processor-radio device 511 can then process the data received from each accelerometer and then radio aggregate kinematic data to the follower (or to multiple followers). This architecture eliminates all wires on the leader and provides a more reliable system that facilitates attachment of devices to the leader and does not constrain the leader's movement due from interference with wires. Alternatively, the central processor-radio 511 on the leader can be eliminated and each accelerometer-processor-radio device (not shown) worn by the leader could sample the accelerometer data at the sensor and each accelerometer-processor-radio device can independently transmit accelerometer data directly to the central processor radio worn by the follower 521 or to multiple followers. Continuing with the description of the hardware architecture shown in FIG. 5, the configuration for the follower shows a single processor-radio device 521 with all actuators hardwired to the output of the processor. For simplicity, the diagram shows four sets of four actuator devices (e.g. vibrator chips) located on the upper left leg 522, lower left leg 523, upper right leg 524 and lower right leg 525 to direct movement forward, back and side to side for the upper and lower left leg and upper and lower right leg. An alternative example configuration is to eliminate all wires on the follower and locate a processor-radio device at each set of four actuators. The follower's body-worn central processor-radio can then transmit actuation commands to the appropriate processor-actuation device that will then energize the appropriate actuator(s) of the four connected. Similarly, the central processor 521 worn by the follower could be replaced with a processor-radio device located near each set of actuators on the follower. Carrying this example further, the accelerometer-processor-radio worn on the lower left leg of the leader could transmit the lower left leg sensed movement data only to the actuator-processor-radio device worn on the lower left leg of the follower. Similarly, each accelerometer-processor-radio device worn on the leader could wirelessly transmit movement information to the corresponding actuator-processor-radio device on the follower on the same body location. For example, the upper right leg processor-sensor device on the leader transmits movement data to the upper right leg processor-actuator device on the follower and so on for each pair of matching sensor devices and actuator devices on the leader and follower.

Another alternative configuration is to provide a small radio-processor integrated with a single actuator device. Each integrated radio-processor-actuator may receive controlling commands from the leader's body-worn central radio-processor or directly from leader's individual accelerometer-processor-radio devices. The localized process will then proceed to energize the connected actuator as directed. Each processor-radio-actuator device will receive movement information directly from the leader's central processor-radio(s) or from the distributed processor-radio-sensor devices on the leader.

Communications between accelerometer-processor devices and actuator-processor devices may be performed using established wireless communications protocols such as Bluetooth, Bluetooth Low Energy (BLE) or ad hoc mesh networks for example. The above represents several possible hardware architecture configuration and is not intended to limit or exclude alternative hardware architecture configurations that support the core leader-sensing and corresponding follower-actuation functions.

An alternative hardware configuration of actuators for the follower is to incorporate more than four actuators grouped at the location of body segments to be stimulated for movement. For example, 8 or 16 or other number of actuators may be employed. All actuators do not need to be of the same type. For example, four linear resonant actuators (LRA) devices may be evenly spaced between four eccentric micro-motors with each device evenly spaced around the circumference of the body location that may be directed to move. Multiple bands at difference locations may also be employed to insure movement signals are sensed and the correct movement is quickly initiated by the follower. Furthermore, a movement sensor such as a triaxial accelerometer may be integrated with the suite of actuators located on the body location of the follower that may be directed to move. The accelerometer can provide valuable information such as whether the follower has performed the desired motion accurately and at the right time. The accelerometer signal can be used for local feedback control and modulate the actuation of the stimulus signal to help the follower in performing the desired movement. For example, if the accelerometer detect movement has not occurred when the local actuator has been energized, a signal may be sent to the processor to increase the amplitude of the actuation device, increase the duration of actuator being energized or energize additional adjacent actuators. The accelerometer can also provide information to avoid energizing the actuator if it is detected that the follower is already performing the desired movement without the aid of stimulus cues.

Figure 6:
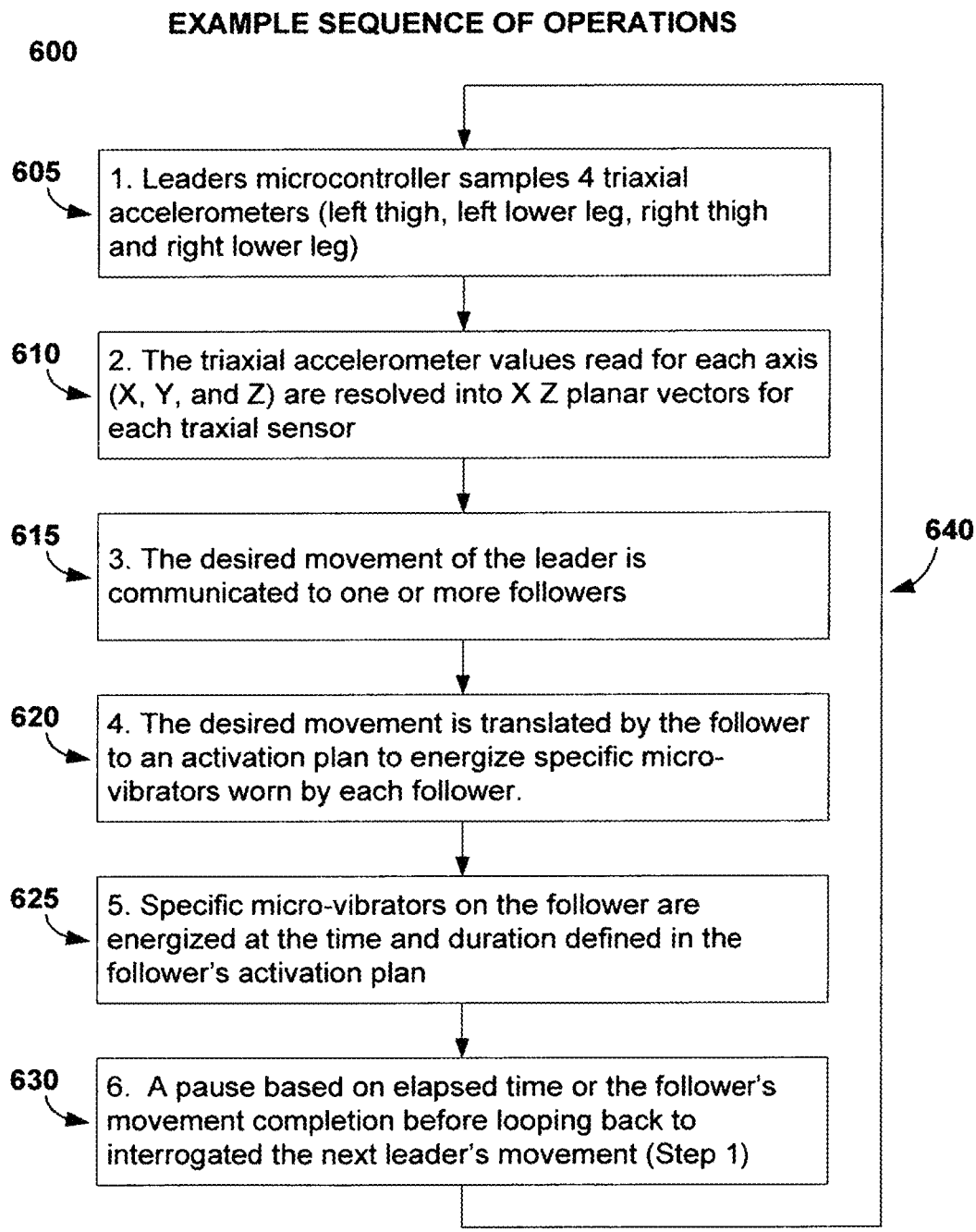
FIG. 6 illustrates an example high-level sequence of steps to direct the movement of both legs for one person, according to an aspect.

FIG. 6 provides an example of the sequence of operations 600 that may be performed using the processors, sensors and actuators depicted in FIG. 5. Movement information is captured by the processor on the leader sampling the movement sensors attached to the leader's legs 605. For simplicity, only upper and lower leg movement is presented in this example. Additionally or alternatively other limbs and body movements may be processed as described in FIG. 6. Continuing with the example, the sampled triaxial accelerometer values are translated to an absolute coordinate system 610 such as the absolute coordinate system described previously. Upon determining the leader's movement in an absolute coordinate system, the leader's movement is communicated to the processor on one or more followers 615. Upon receiving the desired movement information, algorithms in the follower's processor translates the desired movement into an activation plan or timed script that specifies when and how to activate each stimulus device (e.g. micro-vibrator) worn on the follower 620. This activity is performed for each follower receiving the desired movement information 615. The activation plan 620 for each follower is then executed 625. Specific actuation devices are energized at the time and duration specified in the follower's activation plan. As shown in FIG. 6, the sequence of sensing, computing desired movement kinematics, and energizing corresponding actuators is performed iteratively at a specific cycle period. A pause in receiving new leader movement information and responding is implemented 630 may allow time for the follower to carry out the directed motion. This delay also prevents the follower from continually responding to new, possibly spurious movement signals before completing a central, desired movement. The pause or delay may be based on elapsed time (e.g. two seconds) or the follower's completion of the desired movement or the leader's next movement that exceeds a certain movement threshold or any combination of these timing factors for example. Certainly other loop iteration times and actuator duty cycles are possible. For example, the sequence of operation may be interrupt driven with execution of the steps initiated when sufficient movement by the leader is detected. Similarly, the duty cycle of the actuators may change due to many factors such as for example due to the amount of movement needed, the rate of movement needed, observed delay in movement by the follower and the observed error of the follower in performing the desired movement. Upon completion of the movement or time delay for example, the movement iteration loop is repeated 640 and processing then continues back to 605.

Figure 7:
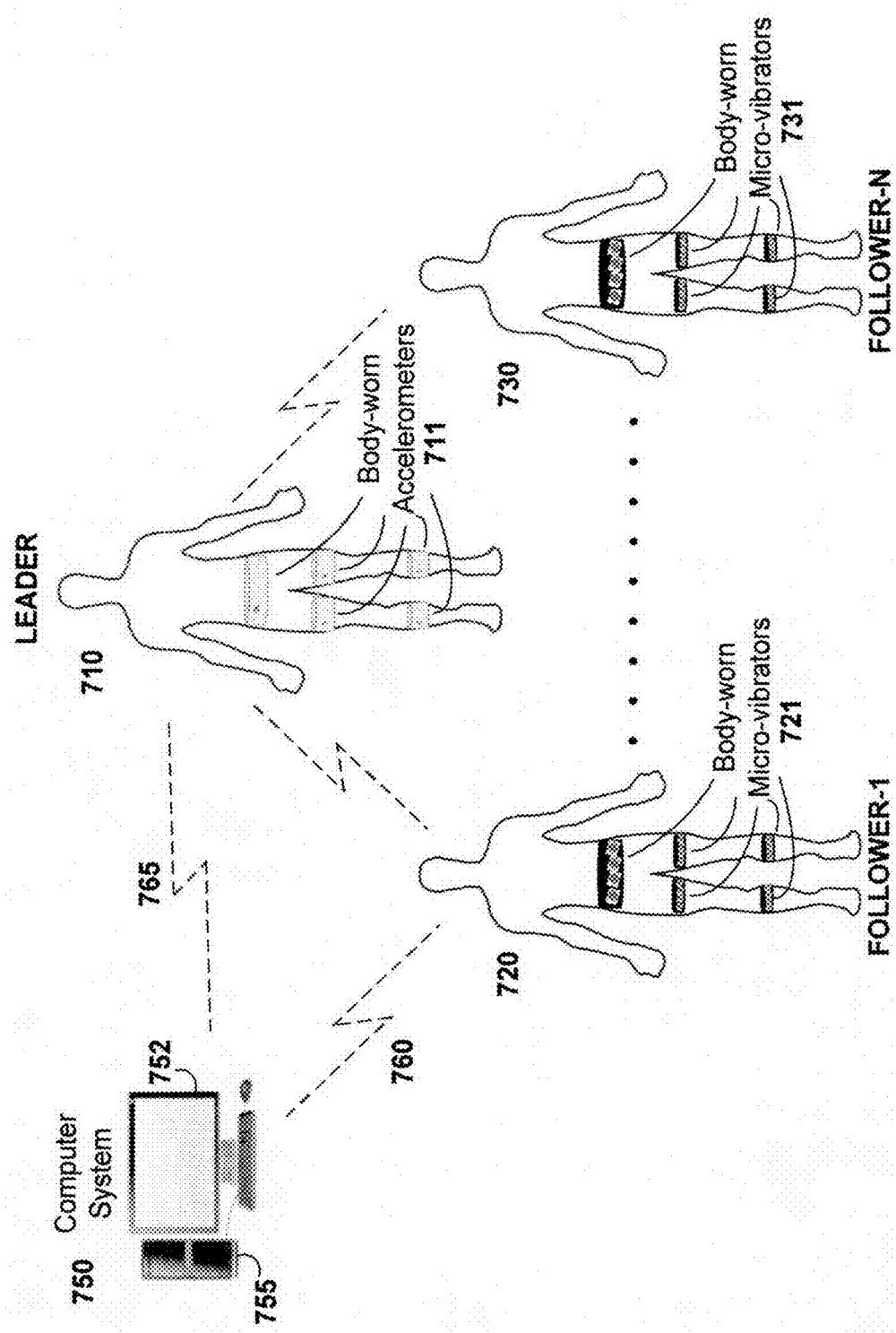
FIG. 7 illustrates an exemplary distributed system that synchronizes the motion of multiple followers with one leader, according to an aspect.

FIG. 7 provides a diagram showing one leader 710 and multiple followers 720 and 730 with body-worn sensors and actuators located on the torso and upper and lower left and right legs. For simplicity the processors, radio, wires, other body-worn sensors and actuators such on the arms, head, shoulders and feet are not shown. Similarly, only 2 followers are shown but clearly there may be only one follower or an arbitrarily larger number, N, of followers may receiving movement signals from a leader. The example configuration in FIG. 7 can support many exercise, therapy, sport training, rehabilitation and dance activities. For example, certain types of surgeries such as coronary artery bypass, heart valve replacement and total hip and knee arthroplasty (THA and TKA) require considerable, specialized recovery therapy. For example, the leader 710 can perform the leg exercised needed for total knee replacement (TKA) while the followers 720 and 730 recovering from TKA receive stimulus signals to perform the same leg movement as the therapist leader.

Also shown in FIG. 7 is a computer system 750 with processor and memory 755, wireless communications 760 and 765 and computer display screen 752. The sensed movement of the leader 710 is determined from body-worn accelerometers 711. The sensed movement is not only transmitted wirelessly to each follower 720 and 730, but the sensed movement is also transmitted concurrently to the computer system 750 via communications link 765 for storage and potential subsequent analysis and later recall.

The bands 721 and 731 shown on the legs and torso of each follower 720 and 730 in FIG. 7 each contain the suite of actuators evenly spaced around the circumference of the body part. Also integrated in each band 721 and 731 on the followers 721 and 731 along with the actuators is a triaxial accelerometer. As stimulus signals are sent to the body part to be moved, the accelerometer at this same location measures the actual movement that occurred. The actual movement that occurred is then transmitted to the computer system 750 via communications link 760 for storage and optionally displayed on monitor 752 for viewing by the leader. In addition to transmitting the actual movement of the follower to computer system 750, the sequence of energizing the actuators may also be transmitted to the computer system 750 for storage and subsequent analysis such as for stimulus-response analysis and potential follower model development.

As shown in FIG. 7, computer system 750 consists of a processor with memory 755, communications links 760 and 765 and video display unit 752. The computer system 750 receives the transmitted leader's 710 desired movement information via communications link 765 and follower's 720 and 730 actual movement information via communications link 760. The video monitor 752 can display observed error of each follower in carrying out the movement directed by the leader 710. When viewed by the leader 710, this may direct the leader to change the type of movement or rate of movement being performed. Additional analysis of the stored leader movement and follower compliance data may be used for example to indicate specific followers having unique movement problems, followers unable to perform some moves or specific weaknesses of a follower, excessive fatigue or indicate a medical problem arising during exercise or dance movement. Analyzing stored movement data of each follower over time can provide useful information about the change in health or rehabilitation success of the follower, the change in movement proficiency of the follower, the ability of the follower to remember movement patterns or combinations of steps or the effect of diet, medication or other lifestyle changes for example.

The example configuration shown in FIG. 7 shows a leader 710 instrumented with body-worn accelerometers 711 and the followers instrumented with body-worn vibration modules and accelerometers 721 and 731. Augmenting the leader's accelerometer bands 711 with a set of vibration modules provides a means of communicating to the leader the error observed in the followers matching the movement of the leader. For example, if followers 720 and 730 often do not step back as far as the leader with their left leg, the vibration device on the back of the left leg of the leader 710 can be briefly energized. In addition, with the leader and follower both instrumented with body-worn accelerometers and vibration modules, it is possible for a follower to switch roles with the leader. The movement of a designated follower will be captured and used to define the activation pattern for vibration modules on the leader and other followers. This may be helpful, for example, for the leader to evaluate the ability of a follower to remember and correctly perform previously performed therapeutic moves, stretching exercises or dance moves. Alternatively, the role of leader may be switch if the leader may be incapable of doing a target movement pattern or a follower may want to demonstrate a new dance step to the leader and other followers.

FIG. 7 shows sensors and actuators attached to the upper and lower legs and torso of the leader 710 and followers 720 and 730. This is an example configuration that may be used for gait therapy or learning dance steps. This configuration can be readily expanded to include additional sensors at other body locations such as upper and lower arms, head, feet hands and shoulders for example. As another example, accelerometers and micro-vibrators could be attached to the wrist, hand and fingers of a leader and followers. Individual finger and wrist movement by the leader may cause stimulus signals at the follower's fingers and wrist causing them to duplicate the leader's movement. Finger and wrist movement by the leader may be performed for therapeutic benefit such as bending and stretching to reduce discomfort from carpal tunnel syndrome. Alternatively, finger, wrist and arm movement could be employed to help a person learn to play a musical instrument such as a saxophone, guitar, drums or piano for example.

Figure 8:
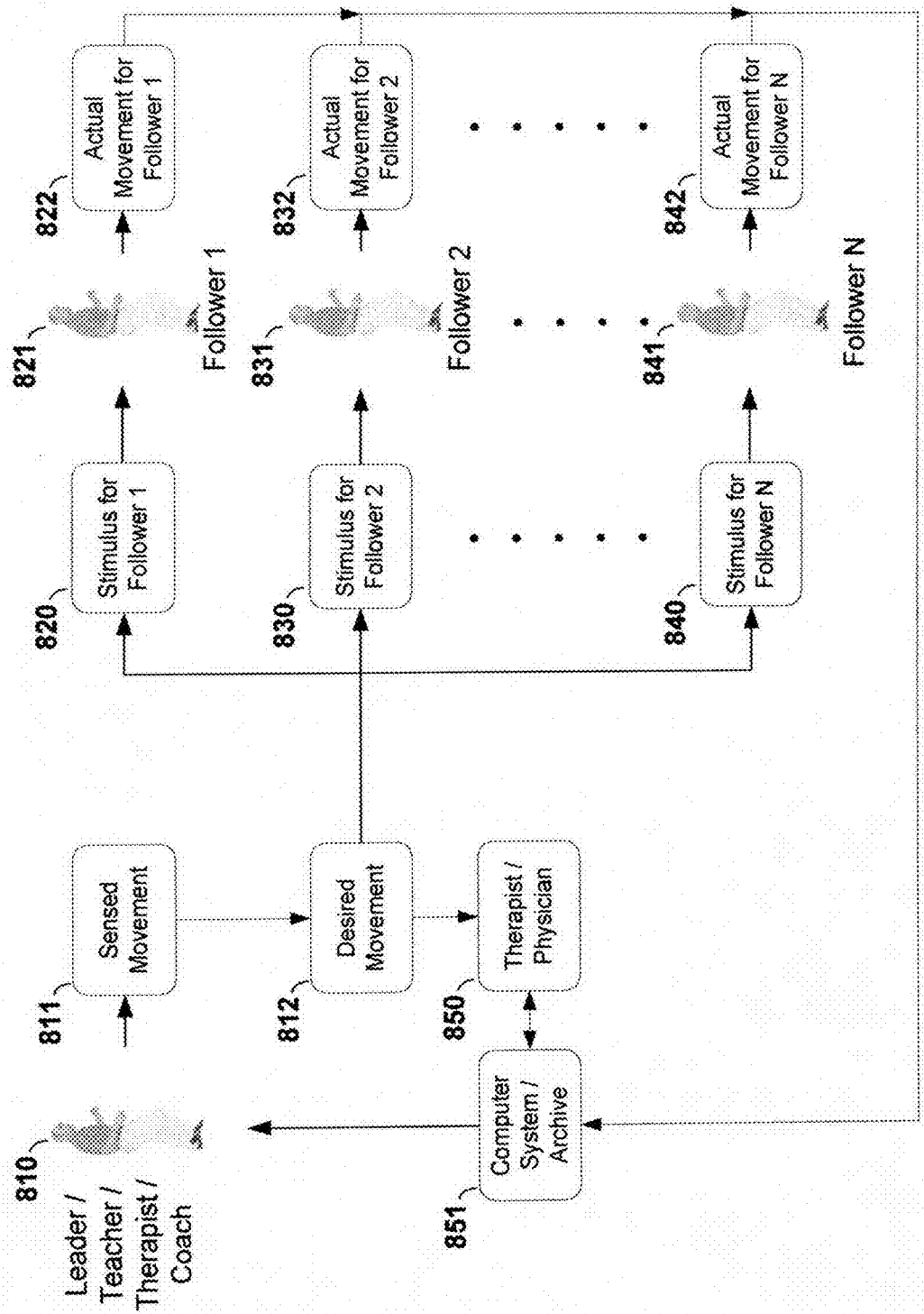
FIG. 8 illustrates an exemplary distributed system that synchronizes motion of multiple followers with each follower's motion monitored, according to an aspect.

FIG. 8 provides a diagram showing a leader 810 and multiple followers 821, 831 and 841. In this example, rather than sending the leader's desired movement 812 directly to each follower for them to duplicate the movement, the desired movement 812 is altered uniquely for each follower 821, 831 and 841 using follower-specific computational processes 820, 830 and 840. A computational process unique for each follower modifies the nominal movement sensed by the leader and adapts this for each follower to accommodate differences in body geometry, skill level, health and cognitive ability for example. Each computational process 820, 830 and 840 is unique to each follower 821, 831 and 841. A model of the follower is integral to each computational process 820, 830 and 840 and is used to alter the movement directed by the leader and transform this to movement that accommodates the unique characteristics of each follower. For example, if the leader takes a step length of 18 inches, this may not be practical for a person of short stature. In this case, the desired movement of 18 inches may be transformed to a movement of only 12 inches for a specific follower. Similarly, a person with motor skill deficits (e.g. a person with Parkinson's disease or multiple sclerosis) the follower-specific computation process may transform the leader's directed movement to a shorter movement and at a slower rate consistent with the physical abilities of the follower. Similarly, a desired step move for a person with Parkinson's disease may be processed to generate a stimulus signal for a short sliding foot move rather than a step with a raised foot to insure a safe move by the follower. As another example, if a follower is recovering from an injury or surgery, the leader's movement may be altered to not only prevent injury but to also facilitate recovery. As yet another example, if a follower is learning a new dance step, the leader's movement may be simplified and the actuators energized to only direct the follower to put the foot in the correct location without regard to foot trajectory, foot travel rate and without regard to arm and body position as directed by the leader. As shown on FIG. 8, the actual movement that occurred 822 832 and 842 for each follower 821, 831 and 841 as a result of their altered stimulus for movement is captured and stored in a computer system 851. Follower response information may be used in the future to adapt the leader's movement commands 812 in the future. Additionally, the desired movement from the leader 812 is stored in a computer along with each follower's response 822, 832 and 842 to the directed movement. The comparison of each follower's movement in response to the directed movement can provide important performance information when reviewed by a therapist or physician 850. This information can help track a follower's performance over time or provide a basis for optimizing future leader moves to optimize benefits for the followers. This information can also be used to track the progress of individuals as well as identify follower weaknesses, health problems or safety issue requiring immediate action for example.

Figure 9:
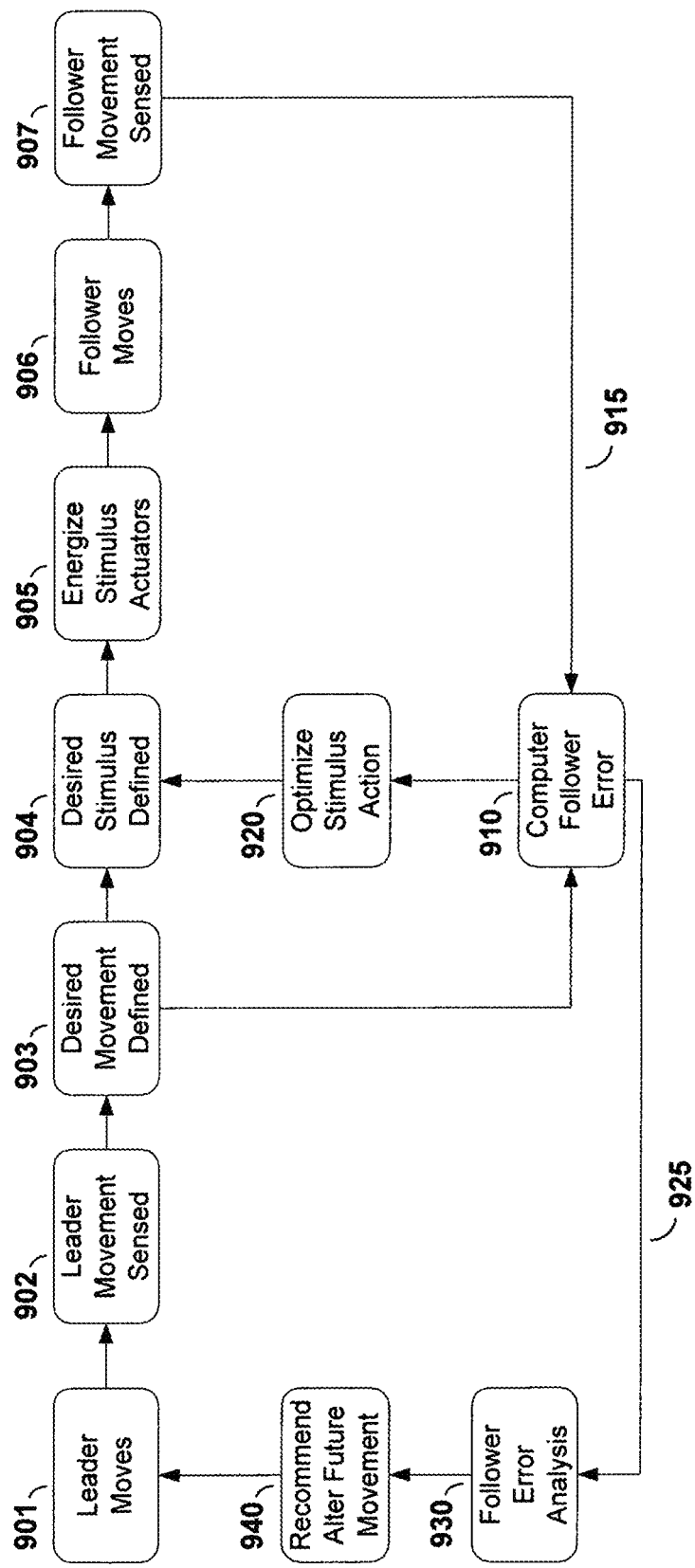
FIG. 9 illustrates a functional diagram of processing steps that employs follower motion feedback to improve movement synchronization, according to an aspect.

Expanding on the use of feedback to aid in future movement by the follower, FIG. 9 provides an example functional diagram showing the steps that may be employed to utilize the follower's response to augment future motion stimulus. In this diagram, the desired movement 903 is determined from the sensed movement 902 of the leader 901. The desired movement 903 is defined and the corresponding stimulus pattern 904 is determined that should cause the desired movement of the follower 906. Upon providing the stimulus 905 to the follower, the follower moves 906 and the actual movement 907 is sensed. The follower's actual movement 915 is compared with the desired movement 903. The difference between the desired movement 903 and the actual movement 915 that occurred is used to calculate the follower movement error 910. The movement error is analyzed and changes may be made optimize the follower's stimulus pattern in the future 920 resulting in changes to the process that determines the desired stimulus 904 for the follower. For example, if the follower's steps are too small and too slow, the next time a step movement is desired, the new adjusted stimulus may results in a stronger stimulus signal, more actuators being energized or actuators energized for a longer period of time. The observed movement error from one or more followers in response to a movement request may be aggregated 925 and analyzed 930. The error from all followers may be communicated back to the leader. A recommendation or algorithm for altering future movement of the leader may be defined 940. The leader may use this information to alter future movement patterns or movement timing for subsequent movement. For example, if most followers exhibit poor accuracy in duplicating the leader's movement (e.g. inadequate step size) is observed 930, a recommendation can be made 940 for the leader 901 to repeat movements until a sufficient number of followers can adequately duplicate the desired movement. Alternatively, if poor movement compliance is observed, the leader 901 may perform the same steps but at progressively slower rates and smaller step size until an acceptable number of followers can duplicate the desired step. If movement compliance if very high, the leader 901 may increase the movement rate or introduce more complex movement patterns or more therapeutic movement patterns. There are many reasons followers do not accurately perform the movements directed by the leader. These reasons include poor physical health including muscle weakness, motor skill limitations such as observed with people with Parkinson's disease, Huntington's disease and multiple sclerosis or cognitive deficits for example. The feedback loop that optimizes the generated stimulus pattern for each follower 915 and the feedback loop from all followers back to the leader 925 will help insure greater compliance to directed movement in the future and provide for safer movement by followers along with increased benefit for the follower from more properly performing the chosen exercise, therapy or dance program.

Figure 10:
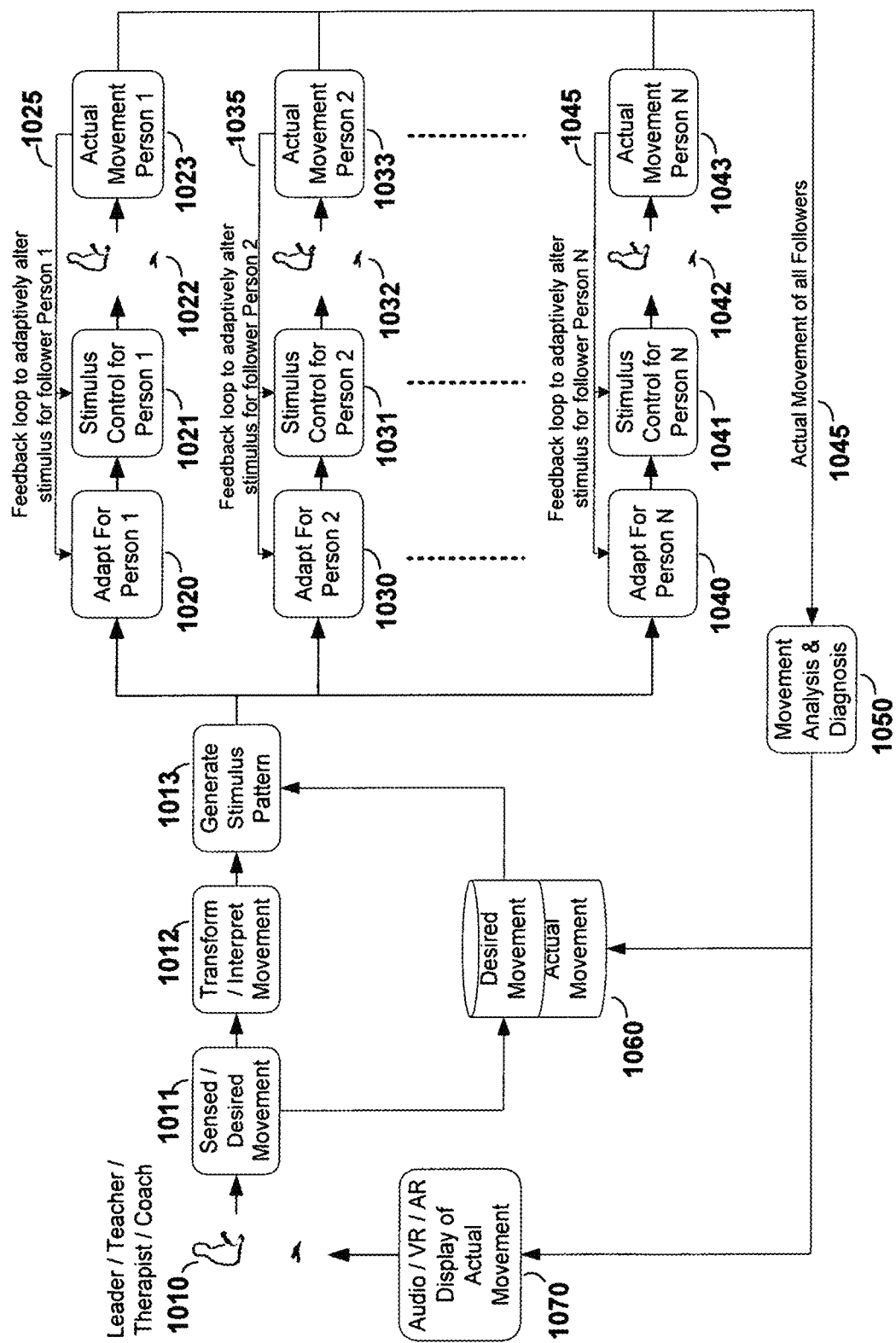
FIG. 10 illustrates an exemplary distributed system employing adaptive stimulus for each follower, according to an aspect.

FIG. 10 expands on the feedback loops presented in FIG. 9 and provides additional detail. The sensed movement 1011 of the leader 1010 is interpreted to generate a desired movement 1012 and a stimulus pattern 1013. The generated stimulus pattern 1013 is then adapted for each follower using an adaptation algorithm 1020, 1030 and 1040 unique for each follower 1022, 1032 and 1042. The adaptation algorithms 1020, 1030 and 1040 each derives a desired movement pattern for each follower 1022, 1032 and 1042 and a corresponding stimulus pattern 1021, 1031 and 1041. Upon energizing vibrator devices according to the stimulus pattern, the actual movement of each follower is measured and recorded 1023, 1033 and 1043. The actual movement observed 1023, 1033 and 1043 for each follower is fed back to the adaptation process for each follower using feedback loops 1025, 1035 and 1045 for each person. The movement adaptation algorithm 1020, 1030 and 1040 for each follower 1022, 1032 and 1042 is altered as necessary to automatically accommodate dynamic changes in the follower's performance and to help insure greater compliance, movement accuracy, therapeutic benefit and movement safety in the future for example.

The algorithms that alter the leader's stimulus signals uniquely for each follower 1020m 1030 and 1040 may include the capability for filtering, scaling, aggregating and deleting some of the leader's movements and transforming them to a series of movements appropriate for each unique follower. The algorithms may be adaptive and alter their operation based on observed changes in the follower's fatigue level, movement accuracy and movement stability for example. Model-based and model-free algorithms such as stochastic methods, analytic models, artificial intelligence, artificial neural nets, fuzzy logic and predictive analytics may be used. Furthermore, a derived set of movement stimulus could be generated and evaluated before using the stimulus pattern to energize actuators on the follower. Generated stimulus patterns may be evaluated before being used for actuation by employing a model of the follower to estimate what the follower's response will be to the planned stimulus activation plan. Based on the results of the model, the actual stimulus signals may be altered again and iteratively evaluated with the model until a desired or optimal set of stimulus signals are derived. One a suitable follower response is predicted using the model of the follower, the desired or optimal stimulus signals may then be sent to the follower and the appropriate stimulus devices energized.

The model of the follower may be adaptive based on the follower's response to a given stimulus pattern. The adaptive model of the follower may incorporate stochastic methods, analytic methods, model-free estimators (e.g. artificial neural nets), state transform methods, adaptive gradient search, linear or non-linear programming methods, adaptive kinetic or kinematic human models or any combinations of these adaptive and predictive methods for example. Iterations of feedback loops 1025, 1035 and 1045 may be performed repeatedly to guide the follower 1022, 1032 and 1042 in performing a desired movement sent by the leader sufficiently close. With each iteration of feedback loops 1025, 1035 and 1045 a model that alters the leader's stimulus signals uniquely for each follower may be changed automatically and adapt to the changing conditions of each follower 1022, 1032 and 1042 such as a gradual increase in fatigue or muscle weakness for example.

One model of follower's performance may be implemented as a state-based model with a linear controller. For simplicity, consider only follower 1022 in FIG. 10 for this discussion noting that the same discussion applies to other followers 1032 and 1042. The state-based model of the movement of follower 1022 will transform stimulus patterns 1013 from movement of leader 1010 to a set of stimulus signals 1021 optimized for follower 1022. If the follower 1022 feedback loop 1025 consistently exhibits delayed movement of the left foot for example, the proportional gain in the model-based linear controller for left foot movement may be gradually increased with each iteration of feedback loop 1025 until the left foot is observed to move adequately for example. Alternatively, or in addition, the model may prescribe that adjacent stimulus devices may be energized to provide a stronger stimulus for movement. A state-based representation of an adaptive kinematic model of follower 1022 that predicts the expected movement of follower 1022 from specific stimulus signals 1021 can be used to efficiently select an optimal gain based on the current fatigue level, cognitive level, health state and motor skill level of follower 1022.

Continuing with the above description using a single follower, 1022, consider another example of model-based transformation of a leader's 1010 desired stimulus pattern 1013 to generate follower-specific stimulus pattern 1021. An alternative follower-specific stimulus transformation model may an artificial neural network (ANN). A multi-layer feed-forward neural network is considered a universal approximator. As such a multi-layer feed-forward neural network can be trained to accurately learn the stimulus-response characteristics of a follower 1022. The ANN can be trained to mimic the stimulus-response characteristics of the follower 1022 using a number of learning methods such as backpropagation. For example, with backpropagation, the artificial neural net is presented exemplars of the stimulus presented to follower 1022 along with the observed movement from follower 1022. After presenting a series of these observations to the neural net, the internal connection weights may be adjusted using established learning methods such a an annealing algorithm, such that when presenting a new set of stimulus-response exemplars from follower 1022, the overall error in predicting the follower's response is minimized. The artificial neural network can continue to learn and adapt to follower 1022. When the ANN is presented a new stimulus signal, the computed output can match the output expected from follower 1022 sufficiently close. The ANN model describing the follower 1022 response to a stimulus pattern permits the stimulus adaptation process 1020 to use the ANN to iterate on a range of possible stimulus patterns and observe the expected follower response until a suitable response is observed from the ANN. The same stimulus that provides the suitable follower response determined from the ANN in 1020 is then sent to the follower 1022 with the expectation that follower will provide an similar, acceptable movement response 1023. The ANN model of the follower 1022 stimulus-response can continue to adapt and track the change in performance of the follower over time using information from feedback loop 1025. The continual adaptation of the ANN to model the follower's performance helps insure the follower-specific stimulus signals will result in the follower duplicating the leader's movement sufficiently accurately while promoting safe movement and accommodating for motor skill limitations of the follower for example. In addition to stimulating movement that sufficiently closely matches the leader movement, additional opportunities exist for optimizing the movement of a follower.

The adaptation of the leader's desired stimulus pattern uniquely for each follower may specified to achieve objectives in addition to or other than closely duplicating the movement of the leader. For example, follower-specific movement stimulus cues may be generated in order to optimize the recovery benefit for the follower from movement for example even if the stimulated movement of the follower deviates substantially from the leader's desired movement. For example, generated stimulus cues to the follower may direct the follower to take a larger step size than taken by the leader in order to safely cause the follower to strengthen certain muscles weakened from surgery thereby optimizing recovery for the follower.

As another example of optimized movement, follower-specific movement stimulus signals may be generated to optimize the therapeutic benefit from movement for the follower. As yet another example, the follower-specific stimulus signals may be generated to promote movement recall by the follower such as to facilitate a follower in learning a combination of exercise moves or dance moves. Continuing with this example, to help a follower learn a movement pattern, the follower-specific movement stimulus signals for a dance sequence may be generated only for the first movement of each step in the combination sequence of steps.

Predictive models such as time-series analysis, health recovery models and time-based artificial neural nets including adaptive predictive models may be employed to optimize the performance, therapeutic benefit, recovery rate or movement memory for example from follower movement. Other optimization techniques such as gradient descent, genetic algorithms and dynamic optimization methods may be employed to optimize the performance of the follower in a goal-directed prescription of movement planning for example. Furthermore, the time scale for optimization may be for the duration of one exercise, training, therapy or dance session for example. The time scale for optimization may also be global and span multiple exercise, training, therapy or dance sessions for example. In this case, it may be acceptable or even desirable to achieve lower levels of performance in a single session. However, over multiple sessions, such as a therapy or recovery period, the follower will achieve superior benefit than by just optimizing individual movement sessions. A technique for achieving optimum follower benefit from multiple sessions is to establish a model that established the expected trajectory of the follower's performance over time from future training or therapy sessions. The performance of the follower is adjusted within each training session to insure the change in performance tracks the expected trajectory of performance improvement sufficiently close. Insuring that the follower's performance matches the time trajectory of performance is achieved even at the expense of accepting deviation from the leader's movement pattern in each session. Deviations from tracking the planned performance trajectory over time may indicate a need for different therapeutic techniques, new movement patterns or a physical or medical problem with the follower for example.

Continuing with FIG. 10, the actual movements observed 1023, 1033 and 1043 for each follower is also fed back 1045 to a feedback control process 1050 for aggregation, error analysis and diagnostics. The desired movement along with the observed movement and movement error for each follower 1060 is stored in memory, a database or file and is also communicated in real time using audio or video techniques 1070 back to the leader 1010. Feedback to the leader will be useful in guiding the leader to alter future movement characteristics such as step distance, movement rate or movement complexity to insure greater effectiveness, safe movement and improved compliance by the followers. Feedback 1070 to the leader 1010 can utilize one or more known methods such as audio, multi-dimensional acoustic, augmented reality (AR), virtual reality (VR), visual graphical display or tactile feedback or a combination of these. For example, vibration actuators attached to the leader in the same location as the accelerometers on the followers could be energized based on the degree of aggregate movement error observed for that appendage on the followers. The vibration signal sensed by the leader could be modulated based on the amount of error or prevalence of error detected in the follower's movement. For example, if followers on average do not take sufficiently large steps back with the right leg to match the leader's step, a vibration stimulus on the back of the right leg of the leader could be energized to signal to the leader that this is a problematic step. The amplitude or duration of the feedback error vibration signal received by the leader 1010 could signal the amount of movement error or prevalence of movement error of right leg movement by the followers. The kinematic movement of the leader and follower may be captured in real time in a computer using the processor, sensor and actuator suite as described in FIG. 10 (not shown here for simplicity). Real time kinematic data can be used to animate an avatar as is done for several motion capture systems commercially available and reference previously. The movement of the leader can be displayed in a virtual reality (VR) image presented to the leader using head-mounted goggles or eyeglasses such as commercially available. A computer-generated avatar of the leader and viewed by the leader can be augmented in a manner to indicate the prevalence, degree and location of movement error exhibited by the followers. For example, the amount of movement error could be exhibited in the VR display seen by the leader as a shadow avatar image near the leader's avatar image that aggregates the error of the limbs of the follower (s). Optionally the movement error of the followers may be amplified in the VR image to clearly highlight the location and amount of follower movement error occurring. As another example, an avatar of the leader could be displayed to the leader with the color of the leader's animated limbs coded to indicate the location and amount of follower movement error that exists. Real time movement error of the followers may also be presented to the leader or followers using augmented reality (AR). AR display of movement and movement performance may be implemented using established viewing devices and computer display and image integration algorithms.

An AR view presented to the leader may superimpose the observed movement error of each follower on the actual viewed image of the follower. For example, the leader may view a specific follower using a head-worn AR viewing device. The specific follower may appear superimposed with a colorized limb or limbs with optional text or icons may indicating the location and character of the movement the follower being viewed is exhibiting. Movement errors may be averaged and only average or maximum error information may be incorporated in the AR display. As the leader looks around the room using the AR viewing device, followers with color-coded error values superimposed on their image will permit the leader to readily identify the followers with movement difficulties or health problems. The use of VR and AR techniques to monitor the followers can be effective in quickly identifying movement errors and adjusting the movement pattern in real time even if all the followers are not directly in the leader's line of sight. For example, if the leader is in one location and the followers are geographically dispersed in one or more remote locations while performing the leader-directed movement, the leader can view the entire class in the VR display as if the class and leader were co-located. Similarly, followers may also to view an avatar of the leader and optionally themselves and other follower using VR techniques. Additionally, when the follower views their own avatar, their movement error or average movement error may be superimposed on their avatar when viewed in real time.

The motion synchronization configuration consisting of a single leader and one or more followers previously described will be useful for a wide range of movement types such as leader-initiated stretching, exercise, rehabilitation, therapy or line dancing for example. However, there are occasions where several people need to move in a non-identical but complementary manner such as in partnered dancing, therapeutic partnered movement or formation dancing or exercise. The ability to synchronize the motion of a group of followers to two leaders performing different but complementary movement is very useful. For example, many publications have shown significant health benefits of dancing for older adults and for people with neurological conditions such as Parkinson's disease, Alzheimer's and multiple sclerosis. The single-leader configuration can be readily expanded to include more than one leader.

Figure 11:
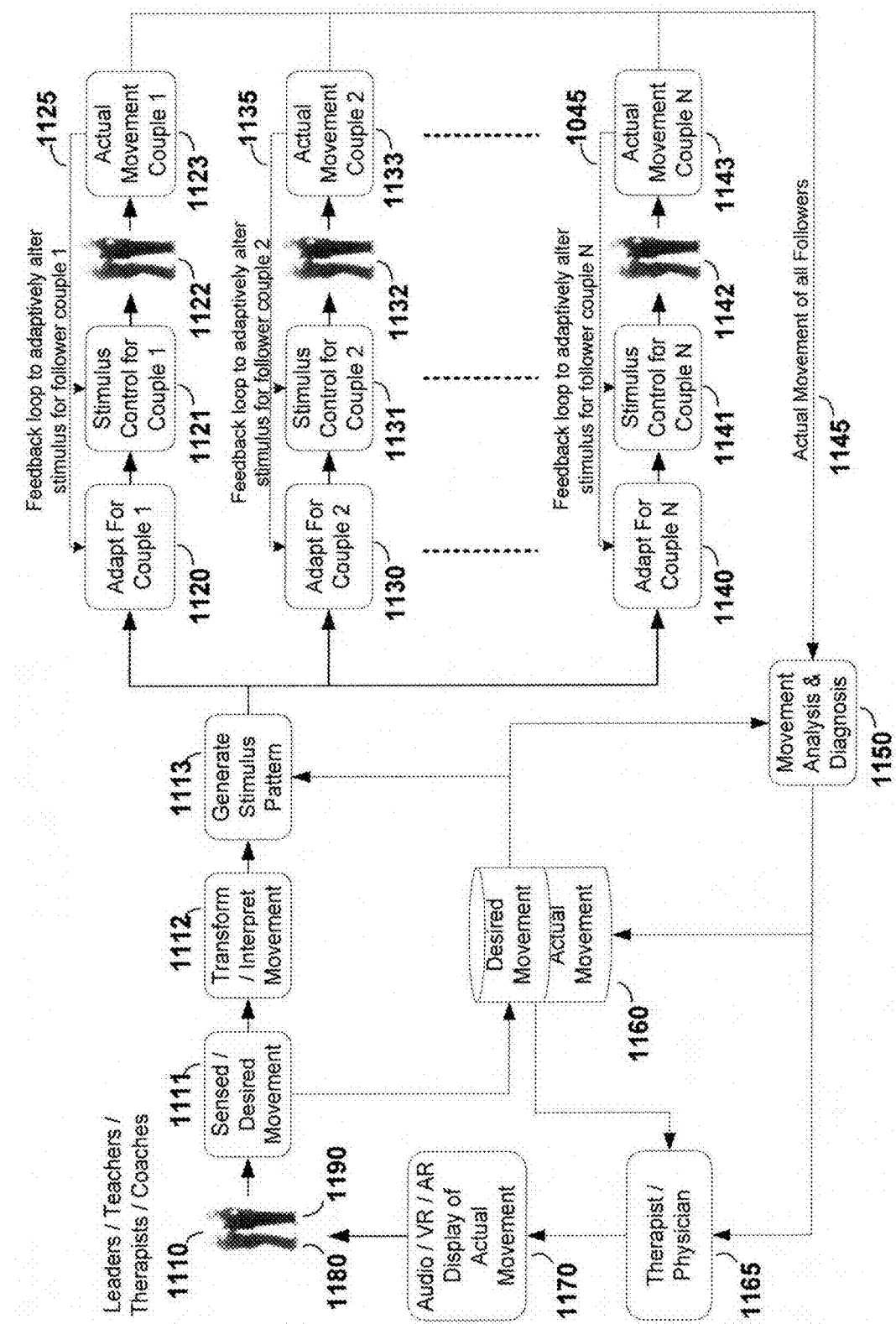
FIG. 11 illustrates an exemplary distributed system with two leaders and pairs of followers, according to an aspect.

FIG. 11 shows an example configuration with two leaders, 1180 and 1190 moving together in a coordinated manner as a couple 1110. Similarly, followers 1122 1132 and 1142 are also pairs of dancers and each dancer in the pair intended to move in a coordinated manner and mirror the movement of their associated partner in the leader couple. This example is representative of partnered ballroom dancing where two dancers form a couple and one dancer in the pair is designated the lead-dancer and the other dancer in the pair is designated the follower-dancer. In partnered dance steps, the leader and follower form a couple and typically mirror each other and perform complementary steps in unison. For example, in partnered dance, typically when one person steps forward with the left foot the partner steps back with the right foot at the same time. For some dance steps, such as the under arm turn, partners perform different non-mirroring step patterns at the same time. The motion synchronization configuration in FIG. 11 can accommodate both people in the pair performing identical steps, performing complimentary steps or doing totally different steps together. In this example, the leader couple 1110, one person is designated the lead-dancer 1180 and the other person is designated the follower-dancer 1190. Similarly, each pair of followers 1122, 1132 and 1142, one person in each follower couple is designated the lead-dancer and the other person is designated the follower-dancer. Lead-dancer and follower-dancer are present in each follower pair 1122, 1132 and 1142 but not specifically identified in FIG. 11 for simplicity. Movement of the lead-dancer 1180 in the pair of leaders 1110 is sensed and the movement captured is kept separate from the movement sensed and captured by the follower-dancer in the pair of leaders. Captured movement data from each leader 1111 is processed in parallel and kept separate (leader-dancer movement and follower-dancer movement). Within the group of followers 1122, 1132 and 1142, the only the lead-dancer in each follower pair receives the movement stimulus 1113 generated from the lead-dancer in the leader pair. Similarly, only the follower-dancer in each pair of followers receive the stimulus pattern generated 1113 generated from the movement of the follower-dancer in the leader pair. Movement error for the lead-dancer and follower-dancer in each pair of followers is measured 1123, 1133 and 1143 and kept separate and used for feedback control 1125, 1135 and 1145 to improve future stimulus signals sent to specific follower dance couples. Similarly, feedback from all followers 1145 for both lead-dancer and follower-dancer in each follower pair, is analyzed to determine compliance errors and movement problems 1150. Follower movement error may also be provided to the leader pair 1110 using audio, video, AR or VR techniques as previously described. Follower feedback received by the leader couple 1110 may assist in altering future movement to insure greater compliance, movement safety or therapeutic benefit for example. Additionally, the desired movement 1111 and actual movement from each pair 1160 is compared and analyzed by a physician or therapist 1165 (or corresponding physician or therapist software program) to track the performance improvement or health problems of each person in each follower pair.

An example was provided in FIG. 10 of a single leader configuration as might occur for example in a group therapy, rehabilitation or exercise class. An example was also provided in FIG. 11 of a two-leader configuration as might occur for example in a partnered exercise class or ballroom dance class with partners moving together in a potentially different but complementary manner. There are occasions where a group of more than two leaders will be useful to guide movement of two or more followers. This might occur for example for people learning square dancing, contra-dancing, formation dancing or team sports employing pre-planned formations such as soccer for example. The configuration presented in FIG. 11 can be expanded to accommodate more than two leader individuals within the group of leaders. Specific individuals in the group of followers will be associated with specific individuals in the leader group. Movements, stimulus signals and specific follower movement and performance errors will be track separately and in parallel with other participants in the follower group. Extending this model further, some sports activities (e.g. soccer, cheerleading and formation dances) may require that each person perform a different movement and in coordination with the movement of other people. Mapping each follower to a specific leader person will permit utilizing the same multi-leader configuration described above.

Lastly, it is possible to compute or synthesize a movement pattern even though one of the leaders in the leader pair does not physically exist. As a simple example, in the case of partnered dance as shown in FIG. 11, where one person performs a complementary, mirrored step in response to the partner's step. The movement of one partner, say leader-dancer 1180 can cause the mirrored step of the follower-dancer 1190 to be automatically generated and provided to the followers along with the actual measured step from existing leader 11180. Step processing for a leader pair described in FIG. 11 will proceed with both the actual sensed movement and synthesized mirrored movement proceeding with step 1112 as if both movement patterns were sensed from human leaders. The remaining processing shown in FIG. 11 can proceed as described above.

Carrying this example further, high fidelity kinematic and kinetic models of human movement exist in the field of exercise science and in the field of computer animation. These models can be used to generate step and movement information using a computer-generated model of human movement. The model-derived movement information can be processed as if the data was actually sensed from a human leader or leaders as described for example in FIG. 10 for a single leader or FIG. 11 for a two-leader pair or even for multiple leaders as might occur in learning a soccer formation.

Figure 12:
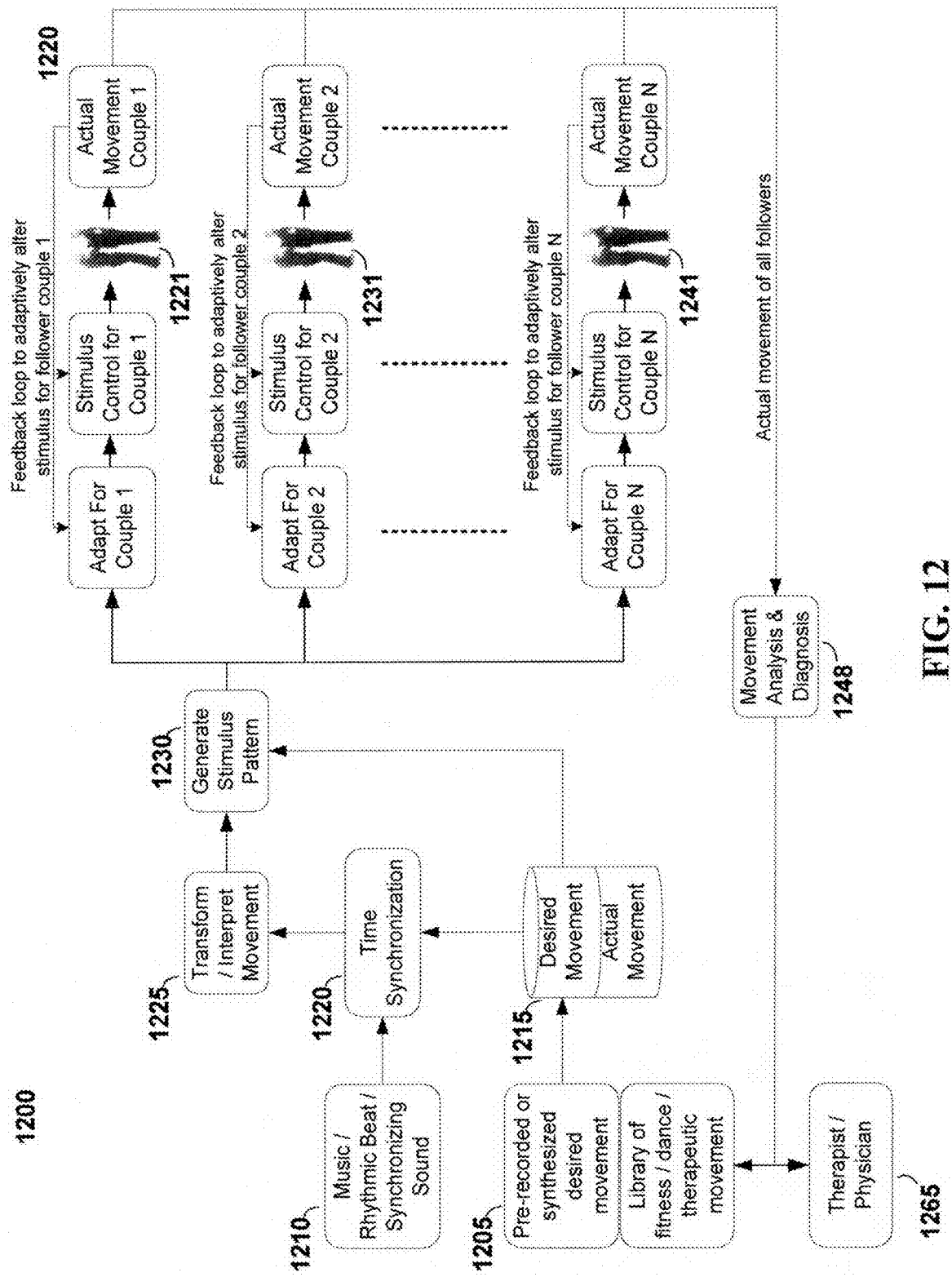
FIG. 12 illustrates an exemplary distributed system with no leaders present and stored movement used to generate stimulus signals, according to an aspect.

The sensed movement of the leaders 1110 is not only communicated to followers in real time 1113 but the same sensed movement of the leader can also be transmitted to a computer and stored in computer memory 1160. Recording the leader's movement is shown at a high level in FIG. 7 and at a more detailed level in FIGS. 10 and 11. Previously recorded movement data from a leader can later be "replayed" and transmitted to followers even though no leader is present. FIG. 12 provides an example 1200 where previously recorded or synthesized movement 1205 is subsequently replayed and communicated to a group of followers 1220. The stimulus pattern 1230 is generated as if the desired movement pattern 1215 was generated in real time from a human leader or from multiple leaders. Additionally, timing information 1220 is added to the desired movement information if it is not stored with the recorded movement data to provide a sequence of desired steps at the same temporal rate as the originally recorded step pattern. Optionally, rhythm music or simply timing beats may be generated or stored. Also, music played during the original recording of the leader's movement may also be stored for later playback along with the movement data. The tempo of the recorded music may be used to synchronize the timing of replayed back movement patterns such as would be useful for performing dance to music. The stimulus sensed from the followers 1221, 1231 and 1241 should sufficiently match the original step pattern provided from the replayed movement data. Other aspects of the system previously described such as real-time motion sampling and movement analysis, error analysis and follower adaptive feedback will proceed as described previously and as if human leaders were present and generating real-time movement patterns and movement cues.

There are important benefits from recording (or synthesizing) leader movement patterns and then replaying the movement script at a later time and generating stimulus signals without requiring a leader to be present. Exercise or therapy classes can be replayed out of a laboratory, clinic or fitness center setting and in a person's home whenever desired and as frequently as desired. Adaptation unique to each follower based on feedback from each follower's performance can still be performed to provide an opportunity to continually improve and benefit from the movement or therapy session. Stored, desired or therapeutic movement sessions and movement details can be readily stored, duplicated, altered, transmitted and later replayed many times by many followers without the requirement to travel to a central location such as a clinic or therapy center. Also, stored movement and music or rhythm tracks can be altered to accommodate changes in the movement performance of the follower. For example as a follower becomes proficient in performing a replayed set of movements, subsequent replays of the same movement can be provided to the follower at an increased tempo and accompanying music or timing cues can have their tempo increased to coincide with the faster rate of presenting movement patterns to the follower. Alternatively, stored movement patterns can be presented to the user at a different rate or to permit exercising or dancing to different music with different tempos. Software exists that can change the frequency of music without changing the tempo. For example, as the follower's proficiency in moving to music improves, the tempo of the stored music and the timing of the movement signals synchronized to music can be increased before sending the movement signals and music to the follower. Additionally, a follower moving to recorded movements and music may get bored or not feel challenged after replaying the same movement script repeatedly. An alternate music track may be substituted for the recorded music and the tempo of the replacement music altered to match the desired step rate for the follower. This can help insure compliance with a therapy or exercise program while keeping the movement patterns changing and interesting. Many videos showing exercise sessions or therapeutic movement are distributed on-line or distributed on media such as DVDs. For example, there are multiple DVDs developed enabling a person with Parkinson's disease to watch the video and perform therapeutic exercises at home. One opportunity is to add a control track to the DVD or multiplex the control signal onto the audio track when the DVD is created. During playback in a person's home, the audio and video is processed as currently done however the control track can be de-multiplexed from the recording track and routed to a microprocessor. The microprocessor can then decode the signal and generate the recorded stimulus signals that will help the follower perform the movements depicted on the DVD.

Additionally, the ability to store leader movement patterns and play back the exercise, therapy or dance session at a later date on demand provides an opportunity to establish a library of movement or exercise sessions. The library of movement sessions may be categorized and include entries for therapy such as for stroke recovery, total hip or total knee arthroplasty (THA or TKA), stroke recovery, Parkinson's disease therapy or therapy for carpal tunnel syndrome for example. For example, the number of THA and TKA patients is expected to grow significantly in the near future due to the aging of "baby boomers", higher rates of arthritis detection and treatment and the growing demand for improved mobility and quality of life. The number of joint replacements will soon make joint replacements the most common elective surgical procedure. Timely, rigorous and patient-directed recovery therapy is critical to the success of joint replacements. The use of library of established effective TKA and THA therapy routines will reduce the delays while waiting for the availability of the therapist and reduce the amount of travel needed by a patient to attend therapy sessions at a hospital or therapy center. Similarly, there is an increase in the number of adults diagnosed with Parkinson's disease and an increase in people diagnosed with Parkinson's disease at younger ages (e.g. early onset Parkinson's disease and young onset Parkinson's disease). Existing fitness and exercise videos use at home by people with Parkinson's can be augmented to provide the associated movement cues while the video is being played. The library of exercise sessions may also leverage the large number of existing exercise and fitness DVDs. A library of ballroom dance steps and routines could be downloaded and assist new dancers or older dancers in learning to dance and enable them to realize the compelling physical and neurological health benefits of dance for example.

Figure 13:
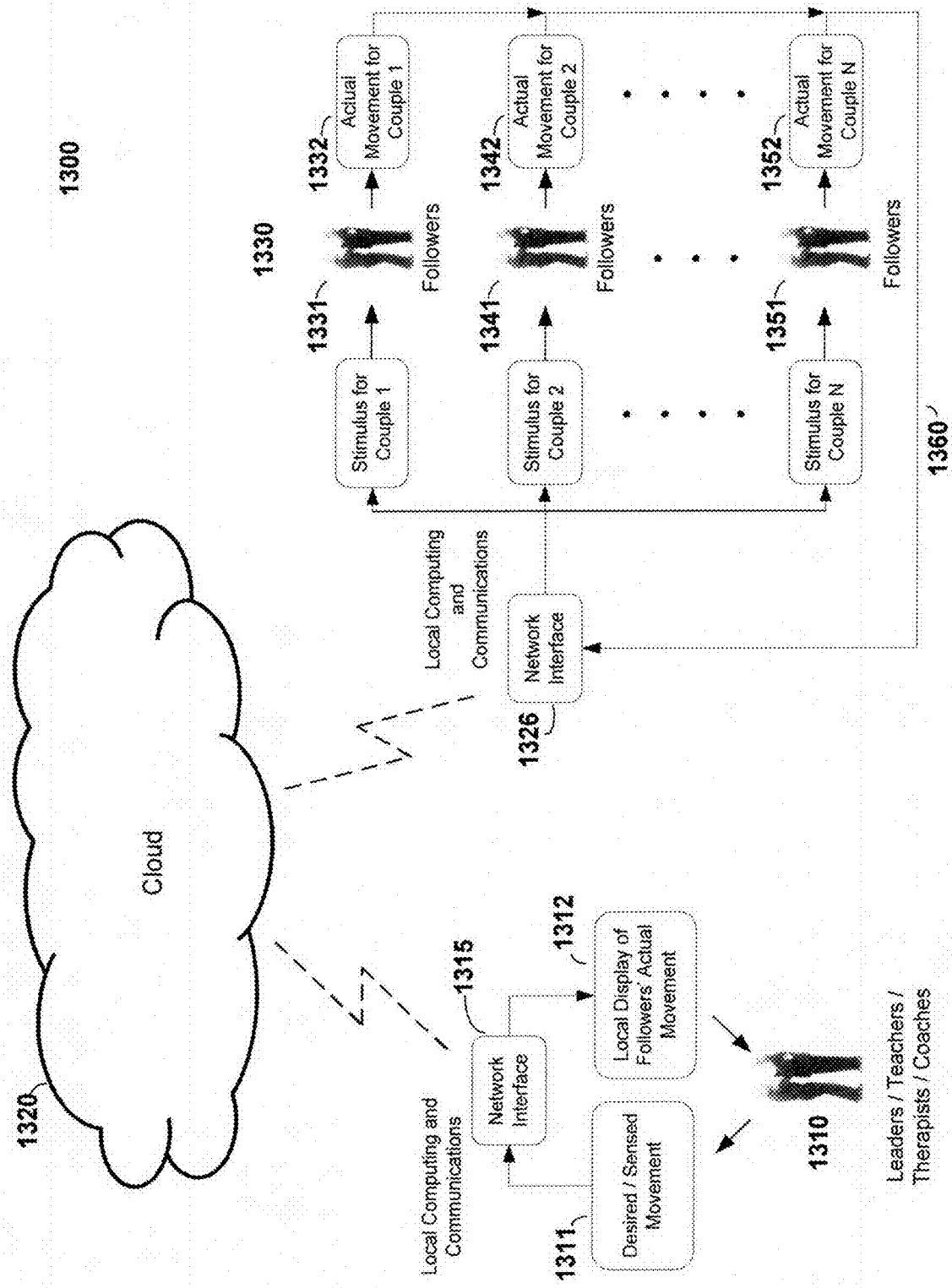
FIG. 13 illustrates an exemplary distributed cloud-based system, according to an aspect.

FIG. 13 shows a cloud-based implementation of the motion synchronization system 1300 that provides for leaders 1310 to be in one location and followers 1331, 1341 and 1351 to be in a geographically different location during an exercise, therapy or dance session. The sense movement 1311 from the leaders 1310 is stored in the cloud 1320 using network interface link 1315. Also linked to the movement synchronization application are followers 1331, 1341 and 1351. Desired movement data in the cloud is transmitted to the followers through the network interface link 1326. Desired movement data from the cloud is transmitted to the followers 1331, 1341 and 1351 and processed locally at the follower's location as if the leaders were physically present and the location of the followers and as if movement data was generated locally in real time. Follower movement stimulus, movement performance and adaptive cueing may be implemented as previously described. In addition, the observed movement of followers 1332, 1342 and 1352 may be combined and detail movement information for all followers 1360 transmitted to the cloud 1320 for storage and subsequent analysis. The actual movement from all followers 1360 stored in the cloud 1320 may be downloaded for local display 1312 by the leaders 1310 using network interface 1315.

The cloud-based implementation of the motion synchronization system facilitates archival storage of movement sessions as well as archival storage of follower response to movement different movement stimulus patterns. Other relevant information of each follower may also be stored with recorded movement data including the movement stimulus they received, their physical size, age, weight, physical health, rehabilitation status and movement objectives. Archived follower information stored in the cloud provides a foundation for tracking a person's change in movement ability, change in health condition and therapeutic effectiveness for example over time and across multiple movement or therapy sessions. Furthermore, archived cloud data facilitates combining the actual stimulus-response from many different followers participating in many different movements sessions to build a robust and efficient empirical model of how a particular follower with certain health conditions or therapeutic needs will respond to a given regimen of leader-directed movement. Furthermore, analytic methods based on big data permits identifying particular correlations and trends not readily visible. Additionally, archived cloud data from movement sessions of different leaders and followers support developing stochastic and analytic models of how followers will response to future movement sessions. Models such as stochastic models, ANNs, analytic models, kinetic-kinematic models, genetic algorithms, fuzzy logic and state-space models for example may be established and adapted using cloud-based archived data. Models derived from cloud data may continue to adapt as additional movement sessions are conducted and follower data including stimulus-response performance is transferred to the cloud for archival storage. Furthermore, the observed change in performance (e.g. accuracy of observed stimulus-response) of many followers with different physical conditions (e.g. Parkinson's disease; Stage Two) reacting to many different stimulus signals across multiple movement sessions permits identifying the movement session(s) and stimulus pattern(s) that historically have provided the most benefit across many similar followers. This information permits establishing an ideal nominal or optimal movement session or stimulus pattern for followers in general and for followers with a given type or health condition. Also, a series of movements sessions that have shown to provide optimal improvement for a follower may be established. Additionally, characteristics of multiple movements sessions that have been shown to be effective may be extracted and used to synthesize a new series of movements that is superior to any specific stored movement sequence. Stored nominal or optimal movement session(s) may be recalled later and used to prescribe an ideal movement session for a new follower. The library of stored ideal nominal or optimal movement patterns will continue to evolve and become more extensive and more effective as leader and follower data continues to be stored in the cloud. Leaders and/or followers may interrogate the cloud-based library and download superior movement patterns or movement sessions to meet movement objectives such as exercise, stroke recovery, dance training or improved gait and balance for Parkinson's.

Figure 14:
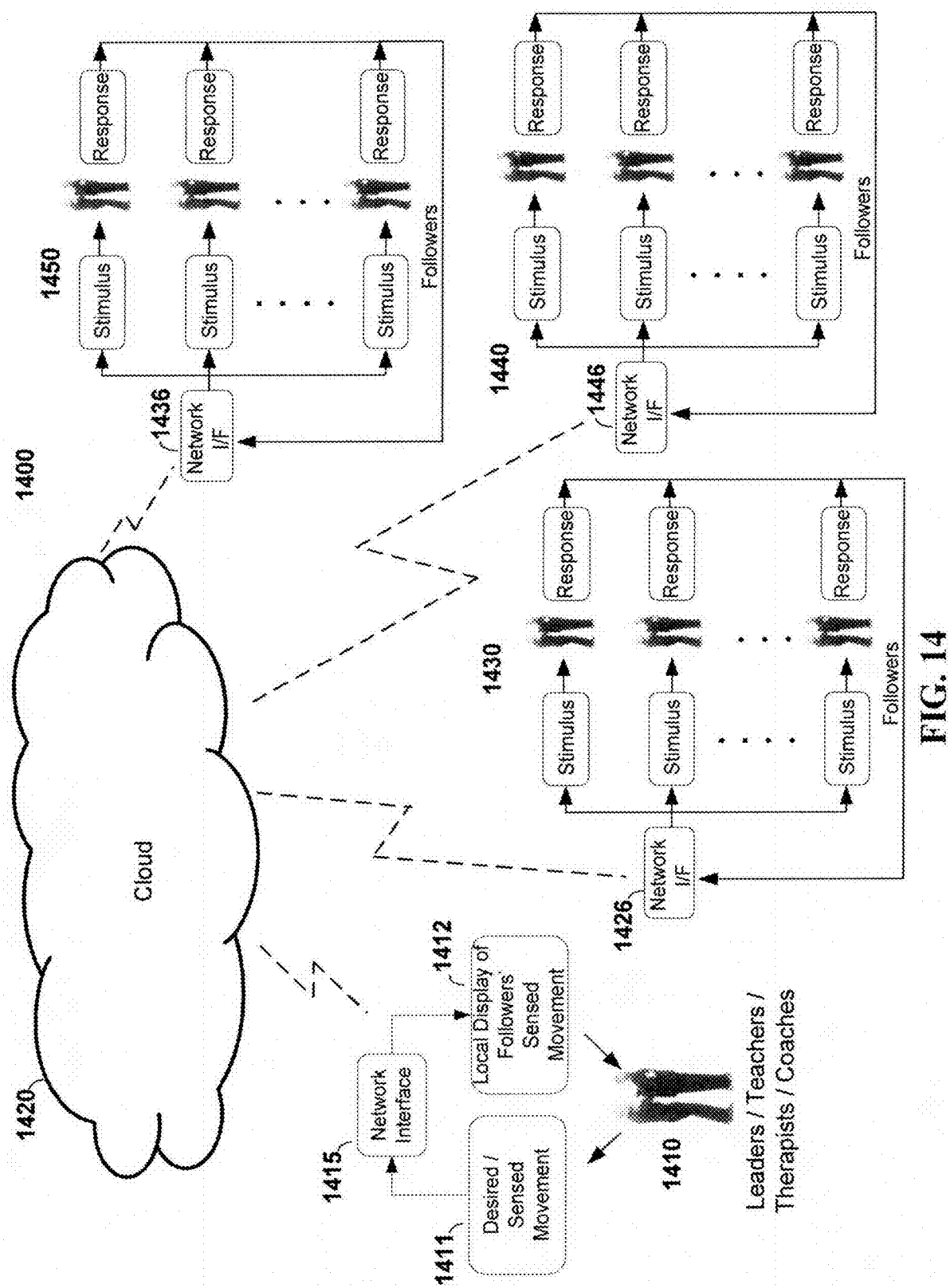
FIG. 14 illustrates an exemplary distributed cloud-based system employing geographically distributed followers, according to an aspect.

Extending the cloud-based movement synchronization paradigm further, system 1400 in FIG. 14 depicts movement data 1411 captured from leaders 1410 being uploaded to the cloud 1420 using a network interface 1415. Multiple follower groups 1430, 1440 and 1450 move to the transmitted movement data obtained from the cloud. Multiple follower groups 1430 1440 and 1450 can concurrently perform therapeutic movement, exercise or dance using movement cues generated from remotely located leaders. Additionally, desired movement data and timing data generated by the leaders and stored in the cloud can be downloaded at a later date. Multiple geographically disperse groups of followers 1430, 1440 and 1450 can download and perform the same of difference movement sessions at the same time or on demand whenever desired. Establishing a library of stored cloud-based movement sessions or series of sessions can proceed as described previously. Similarly, the ability to develop and optimize movement models to meet fitness, therapy, recovery or dance objectives may be performed as previously described.

The cloud-based motion synchronization system implementation shown in FIG. 13 employing a group of followers in one geographic location and FIG. 14 showing multiple groups of follower geographically distributed are representative examples of distributed motion synchronization systems. Other remote computing, distributed computing and cloud-based system configurations are also possible platforms for implementing motion synchronization with one or more distributed leaders in different locations and one or more followers or one or more follower groups in geographically distributed locations. The simple example of a single leader and single follower may also be implemented using a cloud-based architecture similar to the systems described previously.

Figure 15:
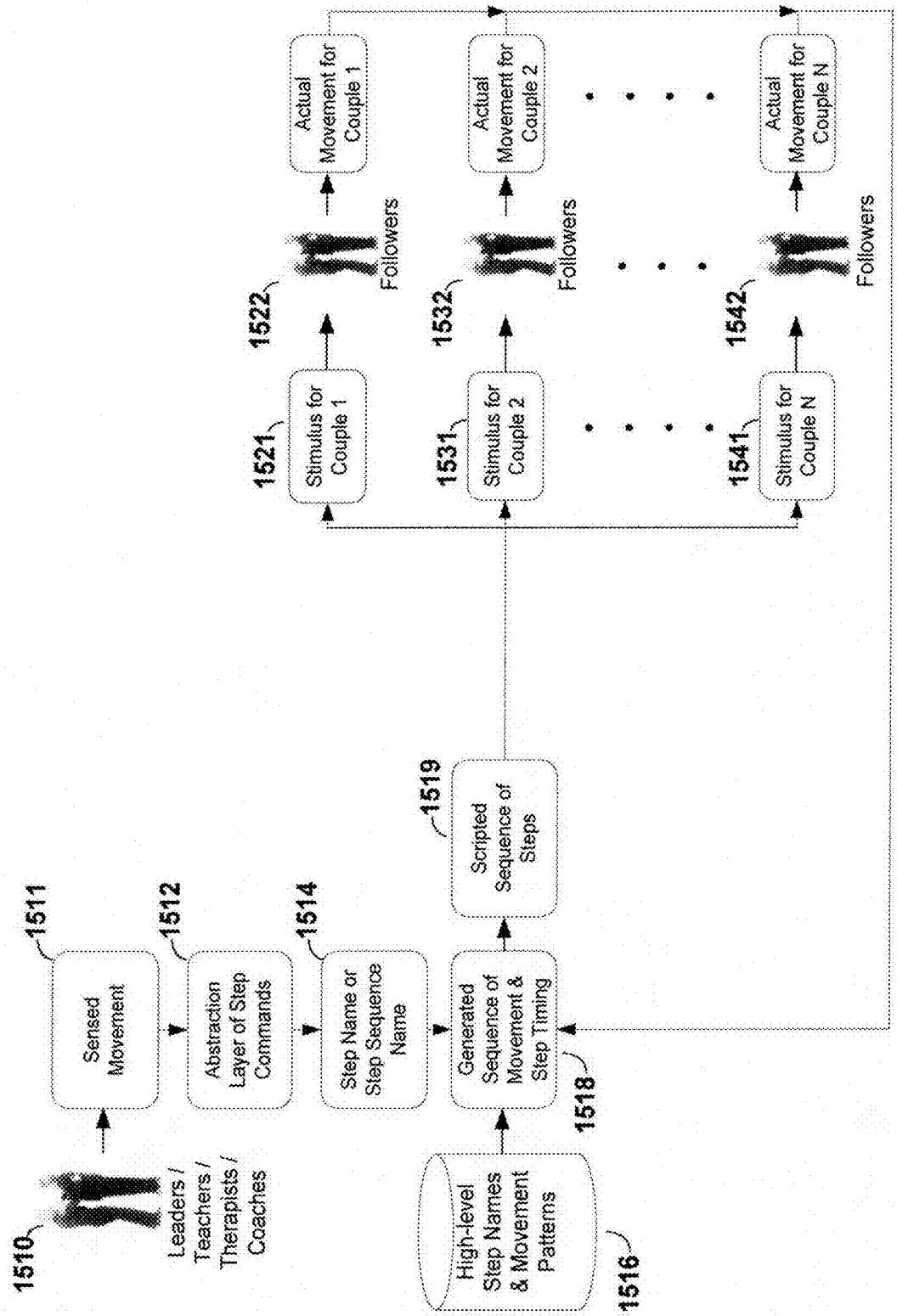
FIG. 15 illustrates an exemplary distributed system employing a higher level command architecture, according to an aspect.

Rather than describing movement patterns of the leader by movement primitives such as leg movement direction and distance obtained from the accelerometer signal, an abstraction or higher-level meta-language may be used to describe a combination of steps. For example, a movement command sequence might be: left foot straight forward then right foot diagonally forward then left foot next to right foot then right foot straight back then left foot to the left and then right foot next to left foot. This series of foot movements may be succinctly described as a "left closed box" step. As shown in FIG. 15, the sensed movement 1511 of leaders 1510 may be analyzed in an abstraction layer 1512 and the sequence of steps analyzed may be associated with a generic or common name 1514. The higher-level step name 1514 may be more meaningful for followers to understand and may promote learning exercise routines and step sequences. Associating a common name with a series of steps will facilitate learning the step sequence and facilitate learning an exercise or dance routine comprised of a series of a few higher-level step names. It will also provide for a more compact representation in computer memory and more efficient communications of movement patterns. The use of an abstraction layer 1512 for defining movement also provides a more concise description of a sequence of steps for the follower to remember and facilitates efficient more adaptation of a sequence of moves for the follower. The use of an abstraction layer 1512 and meta-language for step definition facilitates a precise and consistent script of desired moves to be generated rather than relying on the specific detail body moves and movement primitives generated by a leader. Movement of a leader will vary across leaders and with leaders having different exercise, therapy or dance skills for example. A single leader may have difficulty in closely duplicating movement patterns in different sessions due to human variability of movement, different times of the day and different movement tempos for example. Continuing with the example of the "left closed box", it will be much easier to scale the step size and movement rate of the "left closed box" for a specific follower in a consistent manner rather than performing the adaptation needed for individual discrete steps separately. In addition, the end result may not actually closely resemble a "box" movement pattern stimulus sequence. After adapting the high-level step abstraction and prior to sending the movement directives to the follower, the common step name is "decoded" and the individual movement primitives are then sent to the follower for further adaptation as needed and for directing follower movement. The desired step name can be stored and encoded using a database of step movement sequences 1516. Similarly, the database 1516 can serve to decode a stored movement abstraction and generate the movement primitives that will result in the desired step sequence being performed by the followers 1522, 1532 and 1542.

Figure 16:
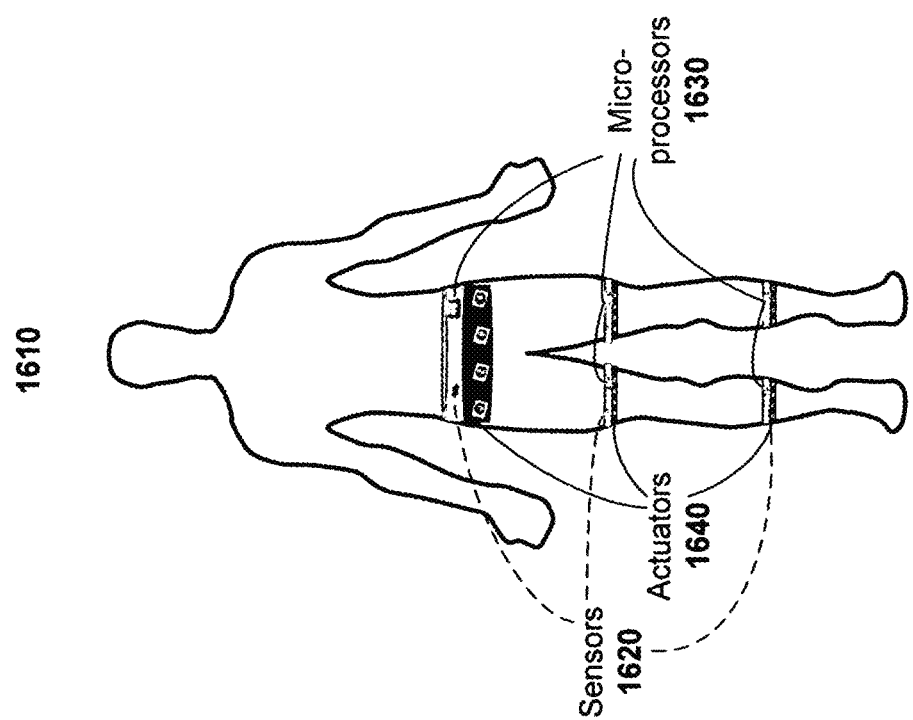
FIG. 16 illustrates a conceptual model of the process with sensors, actuators and processor operable on a single person, according to an aspect.

FIG. 16 illustrates an embodiment of the motion synchronization system where a follower 1610 has multiple bands with each band containing a processor with communications 1630, a sensor such as an accelerometer 1620 and multiple stimulus actuation devices such as micro-vibrators 1640. FIG. 16 provides a simplified diagram of a follower's system configuration and all processors, sensors and actuators shown on the follower are not labeled for simplicity. This is the same configuration shown graphically 720 in FIG. 7 however each band worn in FIG. 1.6 also contains a processor with wireless communications and a motion sensor. Sensing and analyzing movement from a leader (not shown) is central to the movement synchronization system along with providing a specific stimulus pattern to prescribed actuation devices 1640 to direct the follower (wearer) 1610 to move in a specified manner or direction. Analysis software that determines movement error that runs in the body-worn processor 1630 can be enhanced to implement algorithms to determine the movement characteristics of the follower in attempting to duplicate the steps of the leader. The analysis of the follower's movement may not only monitor movement to determine compliance with the leader's directed movement but may also indicate for example a heightened risk of falling such as from a hesitant gait, asymmetric gait or additional steps taken by the follower to regain balance. Algorithms running continuously on processors 1630 can interpret the sensed movement 1620 of the follower 1610 and identify the onset of an unstable gait or unbalance condition. Upon sensing an unstable condition or the heightened risk of falling, an actuation signal can be automatically generated by processors 1630 to energize actuators 1640 in a way that provides a stimulus signal to notify the wearer 1610 of a potential fall so they may focus attention on balance for example and not necessarily on following the leader's moves. Additionally, new stimulus patterns may be generated by processor 1630 to cause actuators 1640 to stimulate the wearer to move in a manner to reduce the risk of falling or move away from an unstable condition. If movement signals continue to be sent from the leader to the follower, under conditions of unstable movement or unsteadiness by the follower, future stimulus signals to support movement synchronization may be aborted or attenuated by processors 1630 to avoid a fall or an unstable condition. Using the wireless communications link, a leader (not shown) can also be informed of the potential for fall or injury of follower 1610. In addition, the corrective action taken by the follower to avoid a fall may also be communicated to the leader or session facilitator.

It is important to insure the safety of a follower that is being induced to move using stimulus signals. Followers performing the directed movement may have diminished motor skills, muscle weakness or reduced cognitive function. All followers must be protected from becoming injured while trying to move in a manner prescribed by the leader. Older adults, people with certain neurological conditions such as Parkinson's disease and people on certain medications are at greater risk of falling. People recovering from injury or surgery may also be at greater risk of falling and subsequent injury. Models that incorporate critical balance, gait and strength variables along with information on age, weight, height, fall history and neurological condition will be the most effective in predicting falls and providing an opportunity to prevent falls. Models may be used to prescribe a movement pattern and set of stimulus signals to cause the wearer to transition to a more stable or safer posture or body motion. These models can also be adaptive and reflect the current energy level and state of alertness of the wearer as well as track the wearer's accuracy in following movement patterns prescribed by the leader. The adaptive models may be resident in one or more processors 1630 and continually adapt to changes in the wearer's 1610 condition and predicted movement patterns. For example, if the center of gravity (COG) of the wearer 1610 is determined to be close to the outside edge of a foot, a stimulus signal may be generated to move the appropriate foot in a manner that shifts COG to a more central location under the wearer's body while all other extraneous stimulus signals are omitted. Suspending movement signals from the leader and entering a "safe" operating mode to insure the safety of the follower can be performed by processors 1630 and be effective in preventing falls and injury from unstable movement or balance difficulties. Alternatively, the wearer may be provided a stimulus signal to reduce lean or slouching thereby providing a more stable base for balance and future moves. Multiple signals may be provided to the wearer to insure timely and safe movement to avoid a fall. Finally, the operating the movement system comprised of sensors 1620, actuators 1640 and processors 1630 can continue to operate iteratively and protect the follower 1610 in the absence of directed movement signals from a leader.

Certain human movement patterns or gait characteristics have been shown to be associated with a greater chance of injury or neuromuscular pain over time or an increased likelihood of future unbalance or falling. Continually monitoring the movement of the follower to insure compliance with leader movements also provides an opportunity for early detection of undesirable movement patterns or gait characteristics. Continual gait monitoring and gait diagnostics is an important capability that can provide for a safer and more beneficial exercise, therapy, rehabilitation or dance session. This capability can be implemented in software using the same processor-sensor-actuator configuration used by the follower for motion synchronization. The follower and/or the leader can be informed of the presence of undesirable movement or gait features using such techniques as an audible cue, actuator stimulus signal, LED illumination or other audio, video or tactile signaling technique. Furthermore, stimulus patterns provided to the wearer can be dynamically altered to direct the person to alter their movement or gait characteristics to a more desirable and safer gait pattern. Continual feedback analyzing gait characteristics and altering the stimulus signal provided to the follower 1610 can help improve the follower's gait over time. For example, stimulus cues may be provided using actuators 1640 to cause the follower 1610 to perform a more symmetric gait by energizing stimulus devices for leg movement that exhibits slow initial movement.

It is significant that the system described in FIG. 16 and the function of gait analysis, gait improvement, fall detection and potential fall prevention can be implemented using the same components used in the motion synchronization system. Furthermore, system operation to insure safe movement can operate in parallel to or independent of the leader-directed motion synchronization system. Local (worn by the follower 1610) computer processing 1630 to identify potential unstable or high risk body motion of the follower can run asynchronously with the leader providing exercise or therapeutic movement stimulus signals. Movement signals from the leader for desired movement may even be suspended or halted while the follower's body worn processor 1630, sensors 1620 and actuators 1640 continue to operate to protect the follower from potential unsafe movement or reduce the risk of falling for example. Detecting the potential for a fall and automatically taking action to energize appropriate stimulus devices 1640 to potentially avoid a fall can operate autonomously on an individual 1610 without the need for a leader, a communications link to a leader or other followers. Similarly, monitoring gait and detecting gait anomalies and providing stimulus signals to improve gait can also operate autonomously on an individual 1610 without the need for a leader, communications link to a leader or other followers. The motion sensors 1620 shown in FIG. 16 can be augmented to include other sensing modalities such as acoustic, ultrasonic, fiber optic, video and infrared (IR) for example. Sensing the approach of an object (e.g. another person, cart or vehicle) can trigger a change in the sequence of stimulus signals to permit the follower to smoothly avoid the obstacle while continuing to walk for example. Similarly, sensing the approach of a curb or step may trigger the upper leg stimulus to actuate to insure the wearer does not trip on a step.

Figure 17:
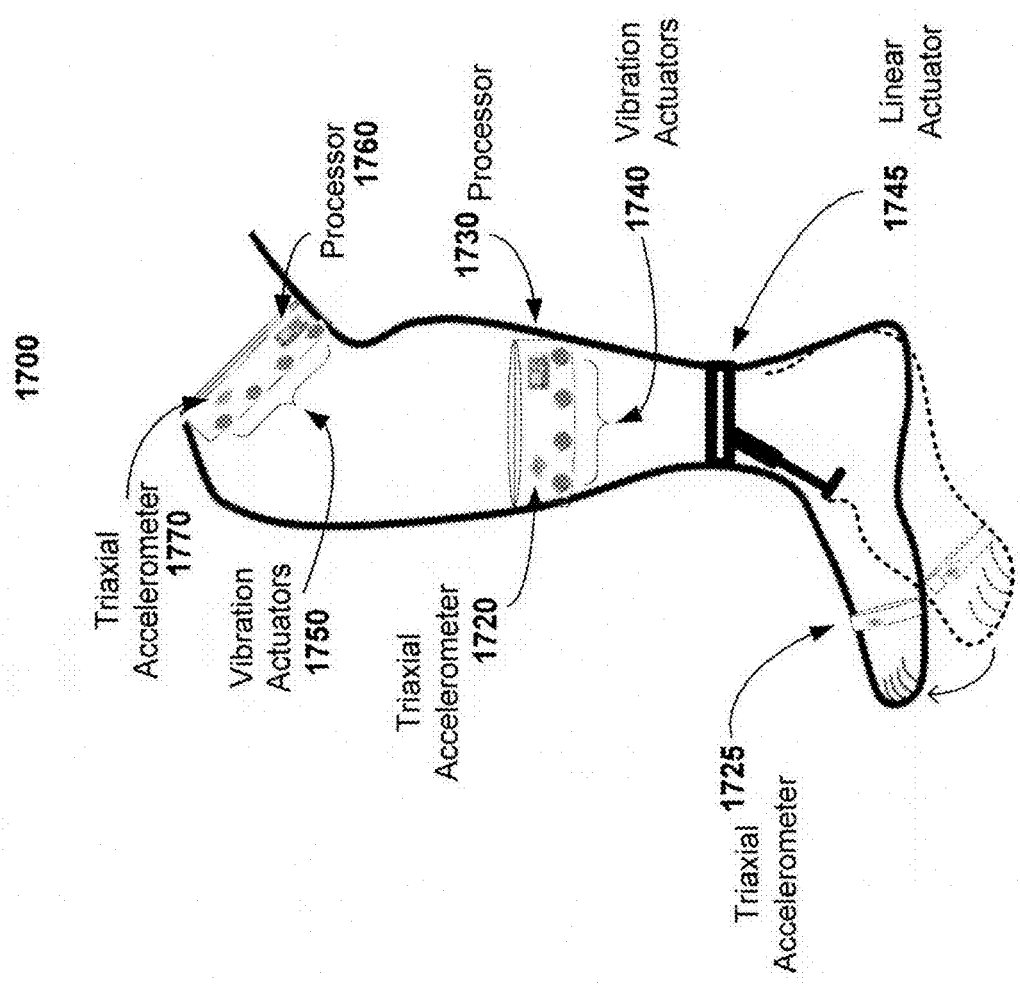
FIG. 17 illustrates a conceptual model of the process with sensors, actuators and processor operable on a single person to actively assist in performing a desired movement, according to an aspect

Continuing with the example of autonomous processing local to the follower to provide compliant motion with the movement of the leader while insuring safe movement and reduced risk of falling, FIG. 17 provides an example of a follower 1700 with muscle weakness or delayed neuromuscular response resulting in a condition known as "foot drop". This condition causes the toes to drag along the ground when stepping and results in a significant increase in the risk of tripping or falling. This condition is found with people suffering from nerve injury or multiple sclerosis for example. The use of actuators that signal the follower to make an appropriate movement (passive signaling) can be extended to include actuators that provide (active) movement assistance for the follower when needed. Additional foot-worn sensors 1725 and actuators 1745 on the follower may provide assistance in performing leader-directed movement while insuring safe movement. For example, if the condition of foot drop on follower 1700 is detected from a foot or shoe-mounted sensor 1725, a signal to energize vibration actuator 1740 may cause the follower to focus attention on stepping and lift the front of the foot resulting in a safer step. Additionally, or alternatively, an actuator 1750 located on the upper leg of the follower may signal the follower to lift the leg higher than required to merely follow the moves of the leader. The higher leg position will minimize the effect of the dropped foot by raising the entire foot and avoid dragging the toes along the ground. Finally, upon sensing a dropped foot condition and an inadequate movement response by the follower, an actuator 1745 (e.g. linear actuator) attached to a shoe brace may be energized and assist the follower in raising the front of the foot and avoid dragging the foot and tripping or falling. This will permit the follower to continue movement in a safe manner. Active movement assistance can be provided to the extent needed to assist the follower in raising the front of the foot. As noted above, sensing the condition of foot drop and responding to protect the follower from unsafe movement can occur autonomously with body-worn processors, sensors and actuators on the follower. Protective and assistive support for the follower can occur between receiving movement direction from the leader as well in the absence of any movement direction from a leader such as when the follower is performing self-directed walking. Gait analysis and protective measures such as assistance in avoiding foot drop can occur continuously.

Figure 18:
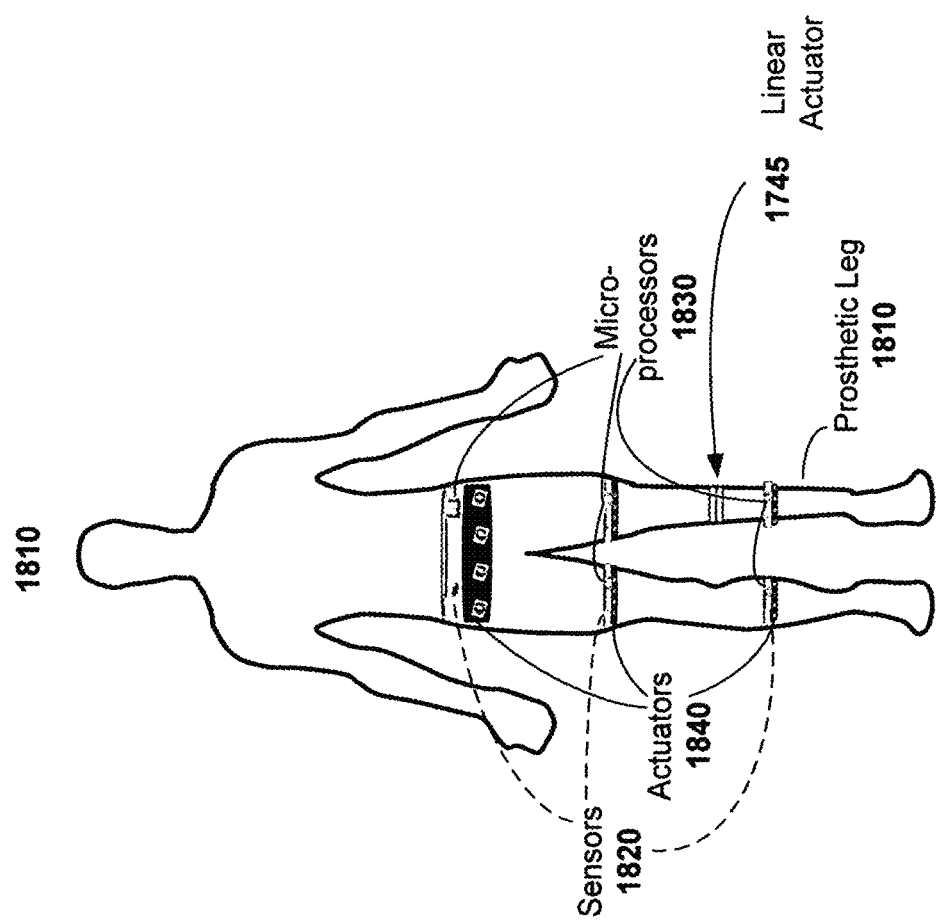
FIG. 18 illustrates a conceptual model of the process with sensors, actuators and processor operable on a single person with a prosthetic limb, according to an aspect.

FIG. 18 continues with the example of actively assisting a follower 1810 in performing movement directed by the leader. In FIG. 18, the follower 1810 has a prosthetic leg 1810 instrumented with a processor with wireless communications 1830, movement sensors 1820 and actuators 1840. Additionally, an actuator 1845 attached to a knee joint on the prosthetic leg (e.g. linear actuator) is capable of assisting the follower in articulating the prosthetic leg. Using upper leg motion, the follower 1810 is able to perform therapeutic, dance or exercise movement similar to the movement prescribed by a leader (not shown) although the movement may not precisely duplicate the movement expected from an able-bodied follower. Upon detecting difficulty in safely performing some of the movement desired by the leader based on input from sensors 1820, active assistance in moving a limb such as the prosthetic leg can be provided using actuator 1845. Based on the amount of assistance needed to insure safe and stable movement, the actuator 1845 can provide a varying amount of assistance up to performing all the movement needed for the prosthetic leg. Similar to the example above, control of the leg actuator(s) may occur in parallel with, or independently of movement requests received from a leader.

General references to body-worn processors or microprocessors or computers imply that communications such as wireless (e.g. Bluetooth) is included along with embedded power, memory, application software programs and firmware. Conventional sensors (e.g. triaxial accelerometer) and actuators (e.g. linear resonant actuators, eccentric balanced micro-motors, linear motors, linear gearmotors) were used to describe the motion synchronization system and the various configurations and options for this system. Alternative sensing, actuation and power components as currently known may also be used in conjunction with or instead of the components referenced in the description of the system. For example, piezo-electric actuators (e.g. stacked piezo-electric structures), pancake motors and micro-linear motors may be used to provide a stimulus to the wearer. Additionally, FES pads or electrodes may be energized in order to assist the follower in performing the desired movement in a safe and reliable manner. Power for operating the body-worn electric components may be provided from conventional storage batteries or from thick film "printed" batteries. Power may also be generated on the wearer using movement such as from the flexing of piezo-electric fiber embedded in shoes or other garments or from the movement of magnet-coil generators. Similarly, the sensors and actuators may be embedded in the wearer's clothing such as socks, shoes or belt for example.

To the extent that the term "includes" is used in either the detailed description or the claims, such term is intended to be inclusive in a manner similar to the term "comprising" as "comprising" is interpreted when employed as a transitional word in a claim. Furthermore, the term "or" as used in either the detailed description or the claims is intended to mean an inclusive "or" rather than an exclusive "or". That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

What is claimed is:

1. A system that facilitates the coordinated movement of one or more people according to prescribed movement patterns, the system comprising:
   at least one movement detection device and processor configured to measure respective movement of each one or more leaders, and one or more followers comprising;
   at least one stimulus device that stimulates movement of the one or more followers when energized;
   the at least one movement detection device is configured to attached to the one or more leaders;
   at least one component that detects movement of the one or more leaders and transmits the detected movement;
   at least one component that receives communications that includes movement information from the one or more leaders; and
   at least one controller that energizes stimulus devices for the one or more followers in a manner causing the follower to duplicate movement of a leader;

the at least one movement detection device and processor are configured to measure the respective movement of each leader 1 and leader 2 of the one or more leaders and each one or more follower 1 and each one or more follower 2 of the one or more followers;

at least a first stimulus device that stimulates movement of one or more follower 1 when energized;

at least a second stimulus device that stimulates movement of one or more follower 2 when energized;

a first component that detects movement of leader 1 and transmits the detected movement;

a second component that detects movement of leader 2 and transmits the detected movement;

a first component that receives communication that include movement information from leader 1;

a second component that receives communication that include movement information from leader 2;

a first controller that energizes stimulus devices . . . to duplicate the movement of leader 1; and a second controller that energizes stimulus devices . . . to duplicate the movement of leader 2.

2. The system of claim 1, wherein leader 1 physically exists and leader 2 movement is determined using a computer algorithm capable of simulating human movement.

3. The system of claim 1, where software algorithms unique to each one or more follower are used to pre-process movement information received from the one or more leader uniquely assigned to the one or more followers before energizing actuators comprising:

a component that designates at least one assigned leader by assigning one of the one or more leaders to each of the one or more followers;

a component that detects movement of each one or more follower and compares it to the received movement of the assigned leader;

a component that modifies the received movement of the assigned leader based on the comparison of historical detected follower movement and received assigned leader movement;

a component that determines a stimulus pattern based on the received movement of the leader in a manner that will cause the one or more follower to more closely duplicate the movement of the assigned leader; and a controller that energizes stimulus devices according to the determined stimulus pattern causing the one or more follower to more closely duplicate the movement of the assigned leader.

4. The system of claim 1, where each one or more follower has at least one movement detection device and processor configured to measure movement of the one or more followers while responding to stimulus signals received from the leader comprising:

one or more movement detection device configured to be attached to the one or more followers; and the one or more movement detection devices captures follower movement information concurrent with the follower responding to movement signals received from the leader.

5. The system of claim 4, where the detected movement of each one or more follower is compared to the detected movement of a leader and a follower movement error is calculated comprising:

a movement detection device that captures follower movement concurrent with responding to movement signals from a leader;

a component that calculates the difference between the sensed follower movement and the sensed movement of a leader; and a component that uses the difference between the sensed follower movement and the sensed leader movement to calculate a follower movement error.

6. The system of claim 4, where stimulus devices for followers are energized in a manner unique and optimal for the follower in a manner comprising:

a component that implements a feedback loop for the follower that establishes an adaptive response model of the follower defining expected movement resulting from a stimulus pattern;

a component that processes the communicated leader movement using the response model of the follower along with follower health and movement proficiency before energizing stimulus devices;

a controller that energizes stimulus devices for the one or more followers using the processed leader movement in a manner causing the follower to more closely duplicate the movement of a leader.

7. The system of claim 1 where one or more sequence of leader movement information is stored on digital media along with information indicating the intended benefits and/or follower health conditions for each one or more sequence of leader movement information forming a library comprising:

a component that captures and stores one or more sequence of leader movement information on digital media;

a component that determines the intended follower benefits and/or follower health conditions associated with each of the one or more sequence of leader movement information;

a component that stores the intended follower benefits and/or follower health conditions associated with each of the one or more sequence of leader movement information on digital media in searchable form;

a component that retrieves one or more sequence of stored leader movement information based on searching for intended benefits and/or follower health conditions;

a component that initiates movement of one or more followers using the retrieved sequence of leader movement information.

8. The system of claim 1, where the sensed movement of each one or more leaders is analyzed and translated to a higher level of movement abstraction comprising:

a component for analyzing individual leader movement and establishing a higher-level movement abstraction by associating a name to a commonly occurring sequence of steps;

a component for storing and recalling a higher-level abstraction representing a sequence of moves or steps; and a component for decoding a higher-level abstraction representing a sequence of moves or steps into the individual steps or moves that comprise the higher level abstraction.

9. The system of claim 4, where the movement of a follower is detected and follower movement is analyzed based on the movement stimulus received from a leader comprising:

a component that analyzes follower's movement response to movement stimulus signals received;

a component that calculates the temporal and/or spatial difference between the sensed follower movement and the movement stimulus of a leader;

a component that analyzes the difference between the sensed follower's response and the stimulus of a leader to determine movement patterns, gait characteristics, balance condition, fatigue level, cognitive level, movement delays, and motor skill level of the follower;

a component that determines the existence of anomalies in gait or balance, unbalance conditions, increased risk of falling, excessive fatigue or muscle weakness, delayed reaction time or health problems; and a component for notifying a leader or health professional if a health or safety problem is detected.

10. The system of claim 9, where the analysis of follower's movement indicates an unstable condition exists for the follower or there is an increased likelihood of a fall or that a fall is imminent, or there is an increased risk of injury and action is taken to reduce the risk of fall or injury comprising:

a component that dynamically alters or eliminates movement signals received from the leader; and a component that generates a series of stimulus signals to cause the follower to return to a more stable state, safer gait, improved balance or other stimulus to reduce the likelihood of falling.

11. The system where the analysis of follower's movement indicates an unstable condition exists for the follower or there is an increased likelihood of injury or a fall or that a fall is imminent and corrective action is initiated to reduce the likelihood of injury or a fall comprised of:

a component for extracting diagnostic features from follower's captured movement that characterize observed movement;

a component for analyzing extracted diagnostic features and classifying the features corresponding to falling or injury;

a component for estimating the likelihood of a fall or injury from the classified features;

a component to determine if intervening stimulus signals are needed for the follower to safely reduce the risk of falling or injury;

a component that dynamically alters or eliminates movement signals received from the leader; and a component to automatically generate a series of stimulus signals to cause the follower to return to a more stable state, safer gait, improved balance or other stimulus to reduce the likelihood of falling.

12. The system of claim 9, where the analysis of follower movement indicates that gait anomalies exist or a potentially injurious movement pattern is observed or a change in follower health exists and a movement stimulus is generated comprising:

a component that analyzes follower movement to determine the existence of abnormal gait characteristics exist that may result in future injury, high joint stress or excessive strain, or a health problem exists;

a component that alters or eliminates future movement signals received from the leader to protect the health and safety of the follower;

a health expert or leader is notified of problematic movement or health problem determined by analyzing follower movement; and a series of stimulus signals are initiated to cause the follower to return to a safer, more stable gait pattern or to move in a manner that will reduce the chance for injury.

13. The system of claim 12, where a follower exhibits an abnormal gait pattern or unstable motion, stimulus signals are generated to direct a more normal gait and safer movement autonomously without the need for leaders, movement commands or leader communications.

14. The system of claim 13, where an unstable posture is detected or gait freezing is detected or the conditions leading to an unstable posture or gait freezing is detected, stimulus signals may be generated to initiate movement from gait freezing, direct a more normal gait and safer movement to avoid an undesirable and potentially unsafe position in a manner that is autonomous without the need for leaders, movement commands or leader communications.

15. The system of claim 1, wherein at least one or more of motion sensing devices, activation devices, power generation devices, power storage devices, electrical connection devices, computation devices, data storage devices and communications devices are configured to be woven into, fabricated into or attached to items of clothing worn by a one or more leader and for by a one or more follower.

16. The system of claim 1, wherein nominal movement patterns for one or more leaders is synthesized from computer models of human movement performing exercises, therapeutic moves or standard dance steps permitting synthesized movement to be used instead of or along with human leader-generated movements to direct follower movement.

17. The system of claim 4, where follower movement performance including movement accuracy is communicated to physicians, trainers, coaches, instructors or therapists for tracking and analysis.

18. The system of claim 17 wherein where follower movement performance is communicated and analyzed comprising:

a component for communicating follower information including movement accuracy to one or more of physicians, trainers, coaches, instructors, leaders or therapists; and a component for analyzing communicated information for diagnoses and to identify needed medical intervention or prescribe a change in the movement patterns for follower in the future.

19. The system of claim 17, where follower movement performance including movement performance is communicated and analyzed over time comprising:

a component for communicating follower information including movement accuracy to one or more of physicians, trainers, coaches, instructors, leaders or therapists; and a component for tracking and analyzing follower movement information over time to identify trends and to prescribe a change in the movement patterns for the follower in the future in order to optimize, over time, the therapeutic value, strength, flexibility, mobility, rehabilitation, gait, balance or other objective from future movement synchronization sessions.

20. The system of claim 4, where the analysis of follower's movement indicates assistance is needed to enable the follower to duplicate the movement of the leader comprising:

a component that indicates follower is having difficulty duplicating the movement of the leader;

a component that determines the follower is unable to duplicate the movement of the leader without help;

a component that determines actively assisting the follower in duplicating the movement of the leader will be helpful and safe; and a controller capable of actively assisting the follower in duplicating the movement of the leader energizes devices to assist the follower in duplicating the movement of the leader.

21. The system of claim 20, where the analysis of follower's movement indicates assistance is needed to enable the follower to duplicate the movement of the leader comprising:
a component that indicates follower is having difficulty duplicating the movement of the leader;
a component that determines the follower is unable to duplicate the movement of the leader without help;
a component that determines actively assisting the follower in duplicating the movement of the leader will be helpful and safe; and
a controller capable of actively assisting the follower in duplicating the movement of the leader energizes one or more stimulus devices as needed to assist the follower in duplicating the movement of the leader.

22. The system of claim 4, where the analysis of follower's movement indicates an unstable, unsafe or abnormal gait exists that can be made more stable or safer comprising:
a component that analyzes follower's movement and determines that an unstable, unsafe or abnormal gait exists;
a component determines that actively assisting the follower in performing movement in a prescribed manner is will be helpful and safe;
a component that determines that actively assisting the follower in performing movement can help the follower achieve a more stable or safer gait; and
a controller capable of actively assisting the follower in performing the needed movement to achieve a more stable or safer gait is energized to assist the follower in transitioning to a more stable, safer gait.

23. The system of claim 21, where analysis of follower movement indicates a problem called "foot drop" comprising:
a component that determines that energizing stimulus devices will not permit the follower to perform the desired movement in a reliable or safe manner;
a component that determines that actively assisting the follower in flexing the foot at a desired time and manner while the follower moves will be helpful and reduce the chance of injury, tripping or falling; and
a controller capable of energizing an actuator attached to the ankle of the follower energizes the actuator in a manner to assist the follower in flexing the foot a correct amount and at a correct time.

24. The system of claim 4, where the analysis of follower's movement indicates difficulty in duplicating the movement of the leader comprising:
the follower with a prosthetic device that limits the ability to duplicate the leader's movement safely or accurately;
a component that determines follower is unable to perform the movement without assistance;
a component that determines actively assisting the follower by articulating a portion of a prosthetic device be helpful and will increase movement safety and accuracy; and
a controller capable of energizing an actuator attached to a prosthetic device energizes the actuator to assist the follower in duplicating the movement of the leader more reliably and safer.

25. The system of claim 21, where follower movement is self-directed movement and not based on leader directed movement.

26. The system of claim 4 where follower movement information captured concurrent with captured leader movement information is stored for subsequent analysis comprising:
a component for capturing and recording concurrent leader and follower movement information;
a component that calculates the difference between the sensed follower movement information and the sensed leader movement information;
a component that uses the difference between the sensed follower movement information and the sensed movement of a leader movement information to calculate a follower movement error information; and
a component that analyzes captured leader movement, captured follower information and follower movement error information.

27. The system of claim 5 wherein the follower movement error is communicated to one or more leaders and presented at least one of visually, visually, audibly, or haptically.

28. The system of claim 23, where analysis of follower movement indicates a problem called "foot drop" further comprises:
a component that determines that actively assisting the follower in flexing the foot at a prescribed time and manner while the follower moves will be helpful and reduce the chance of injury, tripping or falling; and
a controller capable of energizing an actuator attached to the ankle of the follower energizes the actuator in a manner to assist the follower in flexing the foot the correct amount and at the correct time without the need for leader movement commands or leader communications.

29. The system of claim 24, where the analysis of follower's movement indicates difficulty in moving in a safe and stable manner and a controller capable of energizing an actuator attached to a prosthetic device energizes an actuator connected to the prosthetic device in the manner to assist the follower in moving in a more stable and safer manner without the need for leader movement commands or leader communications.

* * * * *